US006808499B1

(12) United States Patent
Churchill et al.

(10) Patent No.: US 6,808,499 B1
(45) Date of Patent: Oct. 26, 2004

(54) THERAPEUTIC AND DIAGNOSTIC NEEDLING DEVICE AND METHOD

(75) Inventors: David L. Churchill, Burlington, VT (US); Helene M. Langevin, Burlington, VT (US)

(73) Assignee: University of Vermont, Burlington, VT (US)

( * ) Notice: Subject to any disclaimer, the term of this patent is extended or adjusted under 35 U.S.C. 154(b) by 92 days.

(21) Appl. No.: 10/188,213

(22) Filed: Jul. 2, 2002

Related U.S. Application Data

(62) Division of application No. 09/676,304, filed on Sep. 29, 2000, now Pat. No. 6,423,014.

(51) Int. Cl.[7] .......................... A61B 5/103; A61B 5/117

(52) U.S. Cl. ...................................................... 600/587

(58) Field of Search ................................ 600/587, 372, 600/562, 564, 566, 567, 568, 573, 576, 578; 439/482, 820, 909; 606/185, 189; 604/117

(56) References Cited

U.S. PATENT DOCUMENTS 5,482,038 A * 1/1996 Ruff ........................... 600/372
5,968,063 A * 10/1999 Chu et al. .................... 606/185

OTHER PUBLICATIONS

Chen–Yu, Chiang. Peripheral Afferent Pathway For Acupuncture Analgesia. Sceintia Sinica, vol. XVI, No. 2 (Feb. 20, 1973), pp. 210–217.

Liangyue, Deng. *Chinese Acupuncture and Moxibustion*. 1987, pp. 325–327.

*Acupuncture A Comprehensive Text*. Trans. and Ed. by John O'Connor and Dan Bensky. 1987, pp. 409–412.

Acupuncture Anesthesia Department of ShangHai Physiology Research Institute, ZhongHua Medical Journal, 1979, vol. 9, pp. 532–535 (With English Abstract).

* cited by examiner

*Primary Examiner*—Eric F. Winakur
*Assistant Examiner*—Brian Szmal
(74) *Attorney, Agent, or Firm*—Downs Rachlin Martin PLLC; Intellectual Property Technology Law

(57) ABSTRACT

The invention relates to a needling device for mechanically effecting needling procedures according to predetermined parameters and/or measuring the physical and/or electrical characteristics of such needling procedures. The invention also relates to methods of using the invention for mechanically effecting needling procedures according to predetermined parameters and/or measuring the physical and/or electrical characteristics of such needling procedures.

39 Claims, 8 Drawing Sheets

ELECTRONICS SCHEMATIC DIAGRAM

PULL OUT FORCE AT ACUPUNCTURE POINTS AND CONTROL POINTS

Fig. 1 Pullout force at Control Points (CP) vs. Acupuncture Points (AP).

Fig. 2 Pullout force at Control (CP) and Acupuncture Points (AP) with three different needle manipulation types; Insertion only with no rotation (NO), Bi-directional rotation (BI) and Uni-directional rotation (UNI).

THERAPEUTIC AND DIAGNOSTIC NEEDLING DEVICE AND METHOD

PRIOR APPLICATION INFORMATION

This is a divisional application of U.S. patent application Ser. No. 09/676,304 filed Sep. 29, 2000 now U.S. Pat. No. 6,423,014.

U.S. GOVERNMENT RIGHTS

At least a portion of the work described herein was supported by National Institutes of Health Grant #RO1 AT00133-01. The U.S. government may have rights to certain aspects of the invention described herein.

FIELD OF THE INVENTION

The invention relates to a needling device for mechanically effecting needling procedures according to predetermined parameters and/or measuring the physical and/or electrical characteristics of such needling procedures. The invention also relates to methods of using the invention for mechanically effecting needling procedures according to predetermined parameters and/or measuring the physical and/or electrical characteristics of such needling procedures.

BACKGROUND OF THE INVENTION

Despite a paucity of rigorous scientific testing, the alternative medicine industry has rapidly grown into a consumer-driven industry, involving annual spending on the order of $14 billion (32). Many alternative therapies are now covered by health plans and taught in medical schools (2a,22a). Consequently, there is a need for research into alternative therapies to validate alternative treatment methods where such validation is warranted, thereby moving valuable treatment methods from the "alternative medicine" category into mainstream medicine, where they will benefit a larger proportion of society. Additionally, rigorous investigation of the basic mechanisms underlying these treatments will serve to protect the public from fraudulent and ineffective therapies based on false theoretical assumptions.

Proponents of alternative therapies often claim that the beneficial effects of such therapies result from phenomena that are not explainable by the currently accepted scientific paradigm. However, it is clear that many alternative therapies do elicit verifiable therapeutic effects, which are explainable according to modem scientific principles. The failure to elucidate the mechanisms responsible for these effects is primarily due to a lack of rigorous investigation.

Moreover, it is important not to dismiss a priori all alternative therapies on the grounds that they are based on concepts that are not compatible with existing scientific knowledge. Ideas that lay outside of prevailing scientific opinion often spur important advances, and the investigation of alternative therapies can be expected to yield new insights into basic disease processes.

An important aspect of the investigation of alternative therapies is the identification of measurable physiological changes occurring in response to such therapies. Once identified, these physiological changes can be analyzed to determine their relationship to the therapeutic effect. The identification and characterization of such physiological changes is complicated where therapies involve procedures that are difficult to test under double-blind conditions. For example, studies involving alternative therapies are often complicated by placebo responses, which are more pronounced with impressive and exotic treatments (102a).

Acupuncture is a component of a complex therapeutic system that has been used continuously in China for more than 2000 years (15,64,98). Acupuncture has become increasingly popular in the United States and is now performed by thousands of physicians, dentists, acupuncturists and other practitioners. Acupuncture has been investigated more thoroughly than any other alternative therapy; however, much remains unknown regarding the mechanisms that lead to its therapeutic effects (81). In its concluding summary, the 1997 NIH Consensus Development Conference Panel on Acupuncture stated that further research into acupuncture-related biological mechanisms is "not only important for elucidating the phenomena associated with acupuncture, but also has the potential for exploring new pathways in human physiology not previously explored in a systematic manner" (81).

Acupuncture research has focused primarily on the systemic effects of the use of acupuncture for inducing analgesia. Analgesia can be obtained by prolonged electrical stimulation of acupuncture needles (electroacupuncture). Acupuncture analgesia is reported to involve the repetitive stimulation of sensory afferent nerves and activation of endogenous pain modulation systems (76,102). The local effects of acupuncture needling have, on the other hand, so far received very little study.

A number of factors suggest that local mechanisms specific to acupuncture may play an important role in its therapeutic effect. First, acupuncture involves the needling of acupuncture points, which are traditionally described as discrete points on the body where acupuncture needling produces a maximum effect (94b). Second, correct acupuncture needling elicits a characteristic local response termed "de qi." This response is often described as a sensation experienced by the patient. Importantly however, a biomechanical phenomenon occurs at the site of the acupuncture needling simultaneously with this sensation (18). Finally, it appears that this biomechanical phenomenon occurs maximally when acupuncture points are needled, compared with surrounding tissue (93).

Needle Grasp and Needling Sensation

A potentially important local effect of needling techniques, such as those used to effect acupuncture therapy, is needle grasp. For example, during acupuncture treatments, acupuncture needles are inserted into specific points of the body, known as acupuncture points, and are then manipulated to elicit a characteristic needling reaction termed "de qi" is observed (1,7,18,20,33,49,53,93). De qi is considered essential to the correct identification of acupuncture points and to the therapeutic effect of acupuncture (18,23,49,66,93,102).

De qi refers to a physiological phenomenon considered essential to guide the correct localization of acupuncture points and appears to be fundamental to the therapeutic effect of acupuncture (18,23,49,60a,66,93,102). In nearly all styles of acupuncture, both manual and electrical, de qi is elicited by insertion and initial brief manual manipulation of the acupuncture needle (1,18,33,49,53,60a,93,99,101). De qi manifests itself in two distinct manners, referred to herein as the two "components of de qi": needing sensation and needle grasp.

Needling sensation, the subjective component of de qi, consists of the sensations perceived by the patient during the needling procedure. Typically, patients describe sensations of "soreness, numbness, heaviness or distention in the area surrounding the needle" (1,7).

Needle grasp, the objective component of de qi, consists of a change in the mechanical interaction between the needle and surrounding tissue. Needle grasp can be perceived by the patient, but importantly, it also can be directly perceived by the therapist. The therapist perceives de qi as contracting of the tissue around the needle, resulting in increased resistance to further motion of the needle (either axial or rotational). Pulling back on the needle results in a visible upward tenting of the skin and increased resistance to pullout.

Many descriptive terms have been used to convey the acupuncturist's perception of needle grasp both in ancient texts and in publications representing the entire spectrum of modern acupuncture practice including proponents of both manual and electrical needle manipulation methods: "tightening" (93), "contraction" (23,99), "gathering" (23), "rooting" (94), "tenseness" (7,18,60a), "heaviness" (23), "squeezing" (49), "grabbing" (49,102), or "resistance" (23). Vivid descriptions of needle grasp appear in a review of Japanese Acupuncture (23): ". . . What at first feels soft, weak and empty at the tip of the needle will gradually tighten up as qi gathers, and it will feel as if the tissue is contracting, with resistance felt at the tip of the needle;" ". . . the resistance in the skin increases, the needle seems heavier and there is also a feeling of movement. Conversely, when the needle moves freely back and forth as if it were in a piece of tofu, and there is no feeling of movement, qi has yet to arrive;" ". . . a sticky feeling as if stepping into deep mud and being sucked in, or as if one were trying to pick up an upside down umbrella with the handle." Occasionally, this mechanical tissue reaction to acupuncture needling can be so powerful that the needle is described as being ". . . gripped by the skin and often with such force as if held by metal pincers" (99). Such strong needle grasp reactions are often referred to as "stuck needle."

The mechanisms underlying needle grasp have never been investigated quantitatively, although a variety of opinions have been expressed in the literature. Proposed mechanisms include: contraction of skeletal muscle (20,44,49,96,102), elastic fibers (44), or smooth muscle (57), aggregation of "subcutaneous fibrous tissue" (1,7) or perimuscular fascia (58).

Research into the therapeutic effects of acupuncture has been complicated by the heterogeneity of clinical practices now included under the term "acupuncture". Some modern schools use acupuncture principally in the treatment of pain (65). Other schools use acupuncture to treat acute and chronic illnesses, often in conjunction with traditional Chinese herbal medicine (54,62,71). Still other schools use acupuncture to rebalance "energetic" patterns in the body (51,89). The recommendations for acupuncture treatments likewise vary widely: some schools use standardized acupuncture point formulas (2,8) while others emphasize individualized point selection based on a variety of diagnostic and therapeutic systems (23,50,54,71,89,112). Needling techniques also vary in the depth of needle insertion, type of needle stimulation (manual vs. electrical vs. none at all) and duration of stimulation (a few seconds vs. up to 30 minutes).

While most styles of acupuncture involve the insertion of needles at classically defined acupuncture points (1a,6,17, 20a,23,33,50,54,72,82a,89,92,99a,101,111), some modem styles disregard acupuncture points in favor of tender or "trigger" points (4,43). However, a study by Melzack (73) found that the location of approximately 70% of commonly found trigger points corresponded within 3 cm to the location of acupuncture points traditionally used for treating pain.

Needle grasp can be used to determine when to remove the acupuncture needles during treatments that employ brief manual stimulation (99). If the needle is left undisturbed once needle grasp has occurred, the tissues gradually relax and the needle can be removed easily, usually after 10 to 20 minutes. With both manual and electroacupuncture, needling sensation and needle grasp both can be used as guides to judge whether or not a needling technique has been performed correctly. When no response is obtained, reintroducing the needle in a slightly different location (often as little as a few millimeters away) frequently results in a strong needling sensation and needle grasp (93). Some schools use only the needling sensation (66), whereas others consider needle grasp more reliable (93).

Investigations of the mechanism underlying de qi reported so far have focused almost exclusively on needling sensation rather than needle grasp. In a study by Chiang et al (19), the needling sensation felt by the patient was prevented by local infiltration of procaine into the "deep muscular tissues underlying the acupuncture point," reportedly without interfering with the cutaneous sensation, though this last point was not documented quantitatively. In another study by Wang et al (108), recordings were made from microelectrodes placed in the median nerve while manual or electroacupuncture was performed distally. The subjective sensations of "soreness, numbness, aching, heaviness and distention" were respectively correlated with the excitation of different types of afferent nerve fibers. These authors' conclusions therefore rest on the highly subjective distinction between these various adjectives. Vincent et al (104) carefully established a sensation rating scale using 20 different adjectives to describe the acupuncture needling sensation. When this scale was used in an experiment in which human volunteers were needled at acupuncture and non-acupuncture points, no significant difference was found in the adjectives used by patients to describe the needling sensation at acupuncture points compared with control points.

Empirical observation suggests that needle grasp is a time-dependent phenomenon which begins a few seconds after needle insertion and subsides after 10–20 minutes (99). It is therefore likely to be an active event triggered by the needle and not to be simply passive tissue resistance. Moreover, the tissue relaxation occurring after needle grasp can be used to determine the timing of needle removal and is potentially an important factor in the therapeutic effect of acupuncture.

Acupuncture Needling Techniques

Although needle grasp can be observed with simple needle insertion (without further needle stimulation), the amount of tissue reaction appears to be related to the type and amount of needle stimulation.

Brief manual stimulation of acupuncture needles for a few seconds is used in nearly all types of acupuncture (manual and electrical) for the initial identification of each acupuncture point (1,18,33,49,53,93,101). The acupuncturist inserts the acupuncture needle, then applies rapid up and down or rotatory motions to the needle, while observing for signs of de qi. Some acupuncturists principally rely on the needling sensation(66), which requires feedback from the patient. Other acupuncturists consider needle grasp more reliable (93) as a sign of de qi, since it can be observed directly. Many acupuncturists use both.

Once de qi has been elicited, supplementary stimulation may or may not be applied to the needles depending on the style of acupuncture, the type of treatment, and the clinical situation. Acupuncture analgesia (especially for surgical procedures) requires prolonged manual or electrical stimulation of needles, often for up to 30 minutes (2). Some schools of acupuncture remove needles as soon as de qi is observed; others leave needles in place without further stimulation and remove them after a period of time; still others use intermittent manual stimulation to reelicit de qi over the course of 15 to 30 minutes (93,99).

Electroacupuncture is achieved by connecting the needle to an electrostimulation device delivering pulses at frequencies generally ranging from 2 to 200 Hz(101).

The two fundamental manual needle manipulation techniques are: 1) lifting and thrusting (i.e., the needle is moved back and forth along its path of insertion); and 2) twisting and rotating at a constant needle depth. Rotation of the needle can be either unidirectional (rotating in one direction only) or bidirectional (rapid back and forth rotation). Unidirectional rotation can elicit strong needle grasp reactions (often referred to as "stuck needle") that can become painful with excessive prolonged manual or electrical stimulation. Unidirectional rotation is therefore not the method of choice for eliciting de qi in acupuncture analgesia. However, both unidirectional and bidirectional rotation are used in other types of acupuncture treatment (49,53,94,99). When needle stimulation is brief (a few seconds), neither unidirectional nor bidirectional rotation cause significant pain, even when strong needle grasp is elicited. A large number of subtle variations on the basic needle manipulation techniques are described in acupuncture textbooks, along with indications for different pathological conditions (1,7,18,33,53).

Location of Acupuncture Points

There has been an ongoing debate among acupuncturists as to the specificity of the acupuncture points described in the classical Chinese literature (102,103). The traditional theory of acupuncture is based on the premise that there are patterns of energy flow through the body that are essential for health (81). The network of acupuncture points and meridians is the traditional anatomical framework upon which these patterns are drawn. Some acupuncture points are linked together by meridians, while others are "extra" points outside the meridian system. Moreover, some modern acupuncturists use techniques which disregard traditional acupuncture points (4,43).

The traditional Chinese method of locating acupuncture points on the surface of the skin uses references to both anatomical landmarks (such as bony prominences or skin creases) and proportional measurements (based on the width and length of various portions of the body) (16). Within the area delineated by these landmarks, the precise location of the acupuncture point is traditionally determined by gentle palpation. The acupuncturist feels for a slight depression or yielding of the tissues, which the patient often reports as locally tender (23,49,99a,101).

There is a need in the art for a means for quantifying needle grasp, e.g., by measuring the force required to insert a needle into tissue, the force required to pull a needle out tissue or by measuring torque as the needle is rotated. There is a need in the art for a mechanical device, preferably controlled by a computer, that can make accurate and reproducible outcome measurements (e.g., measurements of physical and/or electrical characteristics) relating to needle insertion, manipulation and pullout to enable study of needling techniques in a manner which will eliminate potential sources of investigator bias.

There is a need in the art for a diagnostic instrument for diagnosing conditions associated with tissue pathologies that can be detected by needling techniques using the instrument.

There is a need in the art for a tool that can mechanically insert and manipulate a needle (such as an acupuncture needle), measure the pullout force, measure depth of needle insertion, measure needle rotation torque, and record electromyographic evidence of muscle penetration.

There is a need for a miniaturized needling instrument which is light-weight and easy to operate, which can mimic manual acupuncture technique in a precisely reproducible manner.

There is a need in the art for a means for objectively and quantitatively differentiating acupuncture points from non-acupuncture points.

There is a need in the art for a mechanical needling instrument which can elicit de qi.

BRIEF DESCRIPTION OF THE INVENTION

The invention relates generally to a needling device and to therapeutic, diagnostic, and research methods for using the device.

In one aspect, the invention provides a hand-held needling device for measuring pullout force required to remove a needle from tissue of a subject and/or torque resulting from rotation of a needle in a subject. The device generally comprises a shaft, a needle grip mounted at an end of the shaft, a needle suitable for in vivo use in an animal or a human mounted in the needle grip, and one or more of the following components: (i) a mechanism for providing an output indicative of pullout force coupled to the shaft or the needle grip; and (ii) a mechanism for providing an output indicative of torque caused by rotation of the needle coupled to the shaft or the needle grip.

As an example, the mechanism for measuring pullout force may suitably comprise a spring scale mechanism. The spring scale mechanism may, for example, comprise a spring comprising a first arm extending tangentially from a first end of the spring and a second arm extending tangentially from a second end of the spring, wherein the first and second arms are biased towards one another, the first arm is coupled to a tubular handle through which the shaft is inserted, and the second arm is coupled to the shaft. Alternatively, the spring scale mechanism may comprise a spring joined at an end to a tubular handle wherein an end of the shaft opposite the attachment of the needle mount is inserted first through the spring and then through the tubular handle, and wherein an end of the spring opposite the end joined to the tubular handle is joined to the shaft.

The needling device suitably comprises a mechanism for providing an output indicative of pullout force coupled to the shaft or the needle grip and/or a mechanism for providing an output indicative of torque caused by rotation of the needle coupled to the shaft or the needle grip. Either of these mechanisms may, for example, be a loadcell, and both mechanisms may be provided in a single loadcell.

In a more complex aspect, the invention provides a needling apparatus generally comprising a elongated encasement, a needle mount slidingly mounted within the elongated encasement and adapted to receive and hold a needle, and one or both of the following actuators: (i) a linear actuator mounted within the encasement and adapted to impart linear motion to the needle mount longitudinally, and (ii) a rotary actuator mounted within the encasement and adapted to impart rotational motion to the needle. These actuators may, for example, comprise motors.

In any of the aspects of the invention, the needle mount suitably comprises a quick-release device, such as a collet clamp. The needle mount may, in certain aspects of the invention, be adapted to receive and hold the blunt end of an acupuncture needle. The needle mount is also suitably adapted to establish electrical continuity with the needle such that EMG signals may be detected using the acupuncture needle as an EMG probe. A switch may be provided to establish and break the electrical continuity. An EMG amplifier may be provided to amplify EMG signals for transmission to an analog power meter.

In one aspect, the needling device comprises contacting extension or "foot" at an end of the encasement for resting against a subject to stabilize the device during needle insertion. This extension may suitably comprise a loadsensor for detecting and generating an output indicative of the amount of force with which the needling instrument of the invention is being held against the subject.

In another aspect of the invention, the needling device comprises an activation switch for activating the linear actuator to cause the needle mount to extend axially thereby extending the needle out of an end of the device for insertion into a subject and/or an activation switch for activating the rotary actuator to cause the needle mount to rotate after insertion into a subject. In a related aspect, a single activation switch may be configured such that: (a) when pressed a first time, the linear actuator is activated thereby causing the needle mount to extend longitudinally out of an end of the device for insertion into a subject; and (b) when pressed a second time: (i) the rotary actuator is activated, thereby causing the needle mount to rotate after insertion into a subject; and (ii) the linear actuator is subsequently activated, thereby causing the needle mount to retract longitudinally after completion of rotation. In another related embodiment, the needling device may comprise one or more activation switches configured to provide power to the linear and rotary actuators to sequentially provide the following functions: (a) activation of the linear actuator to cause the needle mount to extend longitudinally forcing the needle out of an end of the device and into a subject; and (b) activation of the rotary actuator to cause the needle mount to unidirectionally or bidirectionally rotate after insertion into a subject; and (c) activation of the linear actuator to cause the needle mount to retract thereby removing the needle from the subject.

In another aspect, the linear actuator comprises a miniature DC servomotor. The motor may, for example, be coupled to the needle mount by a lead screw device. In another aspect, the rotary actuator is a miniature DC servomotor. Either or both the linear and rotary actuators may be configured as a stepper motor, such that its speeds, direction, and distance of travel can be controlled by a computer using an open-loop control system.

In yet another aspect of the invention, the needling instrument comprises a linear variable displacement transducer mounted in the elongated encasement for providing a measure of axial needle position. A uniaxial strain gauge loadcell may also be provided to measure the axial load applied to the needle during both needle insertion and/or needle pullout.

The needling device of the invention may also employ a computerized control system adapted to control the linear and rotary actuators in a manner which permits insertion, manipulation and retraction of a needle held by the needle mount. The computerized control system may, for example, be suitably configured to control insertion, manipulation, and retraction of the needle by one or more activation switches mounted to the needling device.

An activation switch may also be provided to generate a signal instructing the computerized control system to zero the loadcell in its starting position and to begin sampling data.

The computer control system may also be suitably programmed to continuously monitor parameters of needle insertion and to terminate operation of the needling device if one or more parameters exceeds a predetermined threshold. As an example, preferred thresholds include (a) needle being inserted more than about 2 mm deeper than a target depth, and/or (b) a maximum insertion or pullout force reaching 3.9 N.

In a safety aspect of the invention, the needling device may be configured such that the axial travel of the needle grip is limited by mechanical stop. The mechanical stop is conveniently provided by contact of the needle mount with the contacting extension. Moreover, all or substantially all of the electrical components may be powered by one or more low voltage batteries. Electrical connections between the needling device and the control and data acquisition system may suitably incorporate optical isolation amplifiers.

In a method aspect, the needling device is used to effect one or more of the following steps: (i) insert a needle into an acupuncture point of a subject; (ii) manipulate the needle; and (iii) withdraw the needle. These steps may be performed as components of a therapeutic needling regimen. The therapeutic needling preferably elicits needle grasp, and more preferably elicits de qi.

In a related method aspect, the invention relates to a method for diagnosing an adverse medical condition by using the needling instrument to (i) insert a needle into a subject; (ii) manipulate the needle; (iii) withdraw the needle; and (iv) measure physical and/or electrical parameters associated with (b), (ii), and (iii). These steps are not necessarily sequential, since the measuring step may be ongoing throughout the insertion, manipulation and withdrawal steps. The physical and/or electrical parameters may be compared with normal physical and/or electrical parameters; the presence of abnormal physical and/or electrical parameters is indicative of the presence of an adverse medical condition.

In a related aspect, the invention provides a method for obtaining physical and/or electrical data elicited by needling techniques by using the needling device to do one or more of the following: (i) insert a needle into a subject; (ii) manipulate the needle; (iii) withdraw the needle; and (iv) measure physical and/or electrical parameters associated with 44(b), 44(b)(ii), and 44(b)(iii). Here again, the steps are not necessarily sequential, since the measuring step may be ongoing throughout the insertion, manipulation and withdrawal steps.

DETAILED DESCRIPTION OF THE INVENTION

For ease of reference, and not by way of limitation, the detailed description of the invention is divided into the sections that follow.

Needling Instrument of the Invention

The invention provides a novel needling instrument for use in a variety of contexts. The needling device of the invention provides a diagnostic tool for measuring characteristics of pathological tissue, a therapeutic tool for effecting needling techniques and a research tool for studying needling techniques. The needling device of the invention enables reproducible technique, important for each of the foregoing uses, which is not possible using manual methods. For example, the needling device of the invention can be used for precise, controlled needle insertion, rotation and pullout, and for measuring physical and/or electrical parameters of such techniques. When used as a research tool, the instrument of the invention helps to ensure that identical procedure is repeated for each measurement and minimizes the need for investigator blinding.

The needling device can be configured at varying degrees of complexity, from a simple, purely mechanical measuring device (see FIGS. 1A–1C) to a highly complex, computer-controlled research tool (see FIGS. 2A–2C and 3).

Figure 1A:
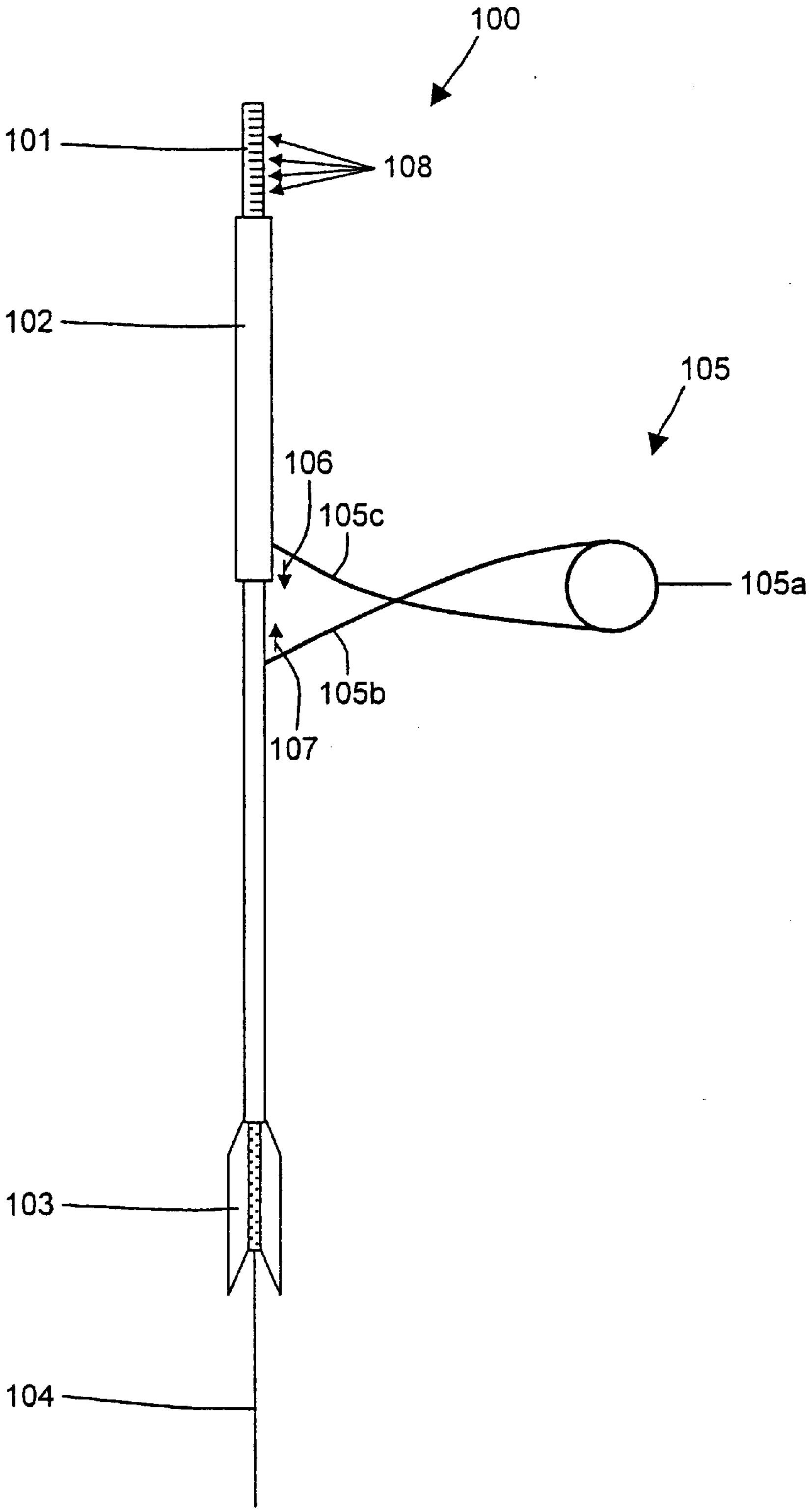
FIGS. 1A–1C show spring scale device representing a less complex embodiment of the invention.
Figure 1B:
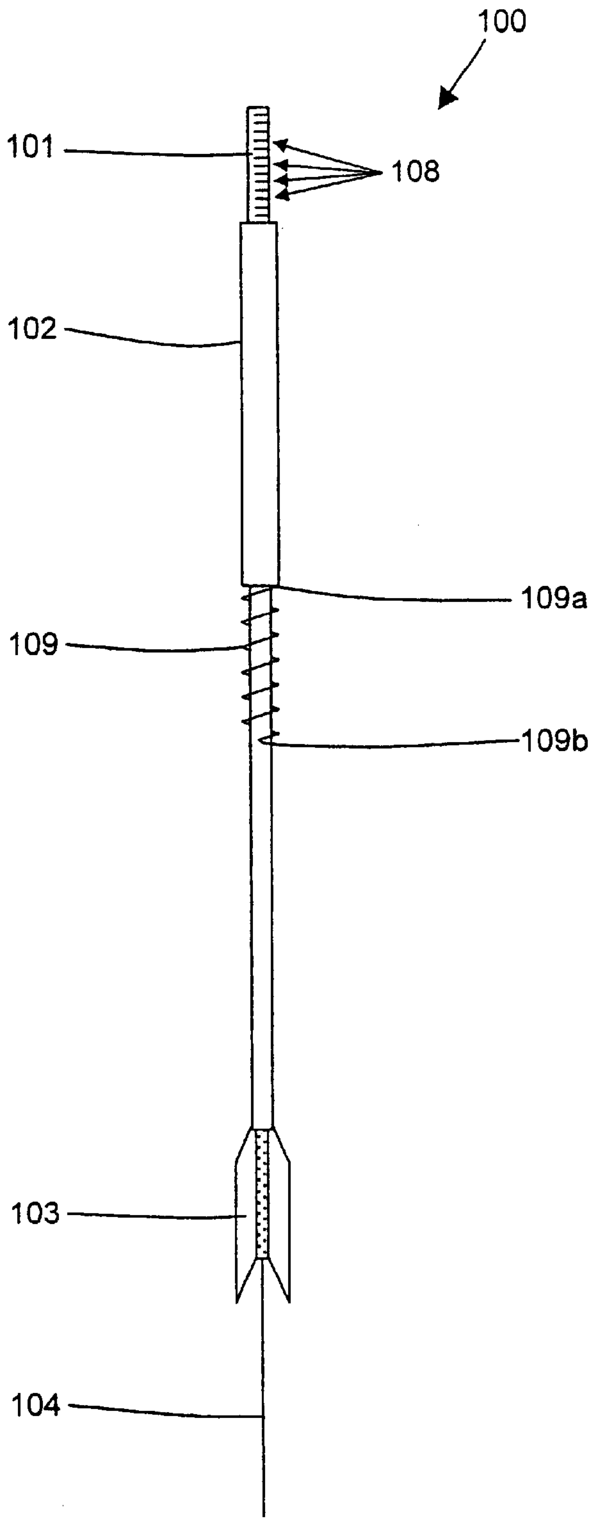
Figure 1C:
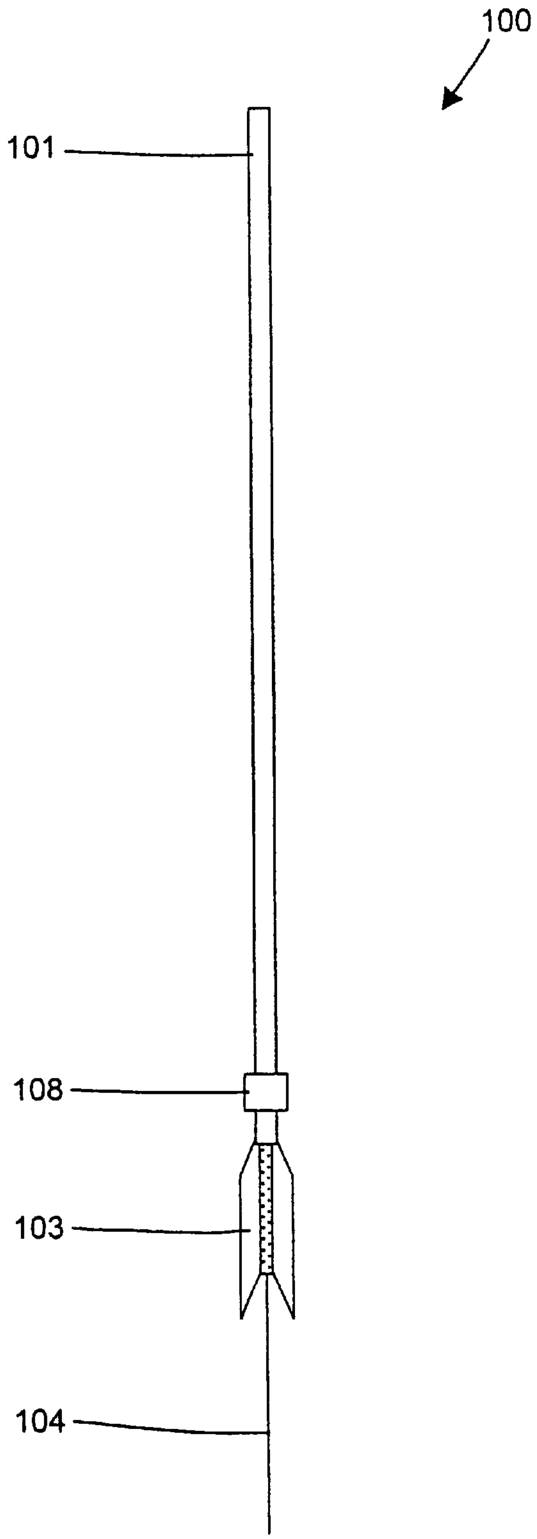

FIGS. 1A and 1B show a spring-scale needling instruments of the invention for measuring pullout force. Referring to FIG. 1A, the device generally includes a shaft 101, a handle 102, which is slidably mounted on the shaft 101. The shaft comprises a needle grip 103 at a lower end thereof for holding a needle 104, such as an acupuncture needle. The handle 102 is suitably joined to the shaft by any mechanism for conferring mechanical resistance to the sliding of the handle 102 on the shaft 101, such that when the needle is inserted in a subject, pulling of the handle will result in the movement of the handle on the shaft. The force required to remove the needle from the subject is proportional to the distance that the handle moves on the shaft. Any mechanism for measuring this movement can be employed to determine the pullout force. For example, as shown in FIGS. 1A and 1B, the shaft 101 may suitably be marked 108 with units of force, so that the force of a pull on the handle is indicated by the mark indicated by the end of the handle 102 or by a projection from the handle 102 or an opening in the handle 102.

The system may also, or alternatively, comprise a loadcell for measuring force, such as hydraulic loadcell that measures compressive loads in terms of fluid pressure. See FIG. 2C for an embodiment of the instrument comprising a loadcell 108 without other means for measuring pullout force. This loadcell may be configured to measure insertion force, pullout force, and torque, or any combination thereof. Moreover, the device may be configured to provide a readout of such force measurements or more simply to provide a readout when a target force is achieved. Thus, for example, the shaft may comprise a light emitting diode that lights up when a predetermined torque is achieved. Such device is useful, for example, in a therapeutic environment to ensure that adequate needle grasp is achieved without harming the subject or causing “stuck needle.” Alternatively, or in addition, the shaft may comprise a light emitting diode that lights up when a predetermined pullout force is achieved, to provide an indicator that adequate needle grasp has been achieved.

In FIG. 1A, the force resistance-conferring mechanism is a spring device 105, comprising a spring mechanism, 105*a*, with two arms, 105*b* and 105*c* extending therefrom. A first arm 105*b* is coupled to the handle 102 to bias the handle 102 towards the needle, as shown by arrow 106. A second arm 105*c* is coupled to the shaft 101 to bias the shaft 101 in a direction which is opposite to the bias of the handle 102, as shown by arrow 107. The strength of the force resistance-conferring mechanism is selected to correspond to the range of forces required to remove a needle from a subject after various manipulations. The second arm 105*c* may be suitably coupled to the shaft 101 to permit the shaft 101 to be rotated, thereby permitting the user to manually perform various rotational needling techniques. Alternatively, the shaft 101 may be separated into two parts below the point of attachment of the second arm 105*a*, to provide a lower shaft component, which is rotatable, and an upper shaft component (including the point of attachment of the second arm 105*a*), which is not rotatable.

Moreover, the apparatus may be readily modified using a device for measuring mechanical force or power transmitted by a rotating shaft 101 to measure the torque of the needle as it is manipulated by the user, e.g., by insertion into a subject and subsequent rotation. For example, the device can be configured to measure torque in terms of the elastic twist of the shaft 101. Moreover, the device may suitably include a torque measuring device 108 inserted between sections of the shaft 101 (e.g., see FIG. 1C), at either end of the shaft 101 (e.g., between the shaft 101 and the needle grip 103), or incorporated into the needle grip. Examples of suitable torque measuring devices include torquemeters, miniature torque transducers, miniature torsion transducers, miniature transmission dynamometers, miniature absorption dynamometers, etc. As another example, a lower portion of the shaft 101 may attached to an upper portion by a means for providing a constant restraint to the turning of the lower portion, e.g., by mechanical friction, fluid friction, or electromagnetic induction, to provide a measurement of torque corresponding to the torque of the needle as it is rotated in the subject.

One of skill in the art will recognize that numerous variations on the basic concept are possible. FIG. 1B shows one such alternative, in which a spring 109 is attached at one end 109*a* to a tubular handle 102 and at another end 109*b* to a shaft 101.

Figures 2A, 2B, 2C:
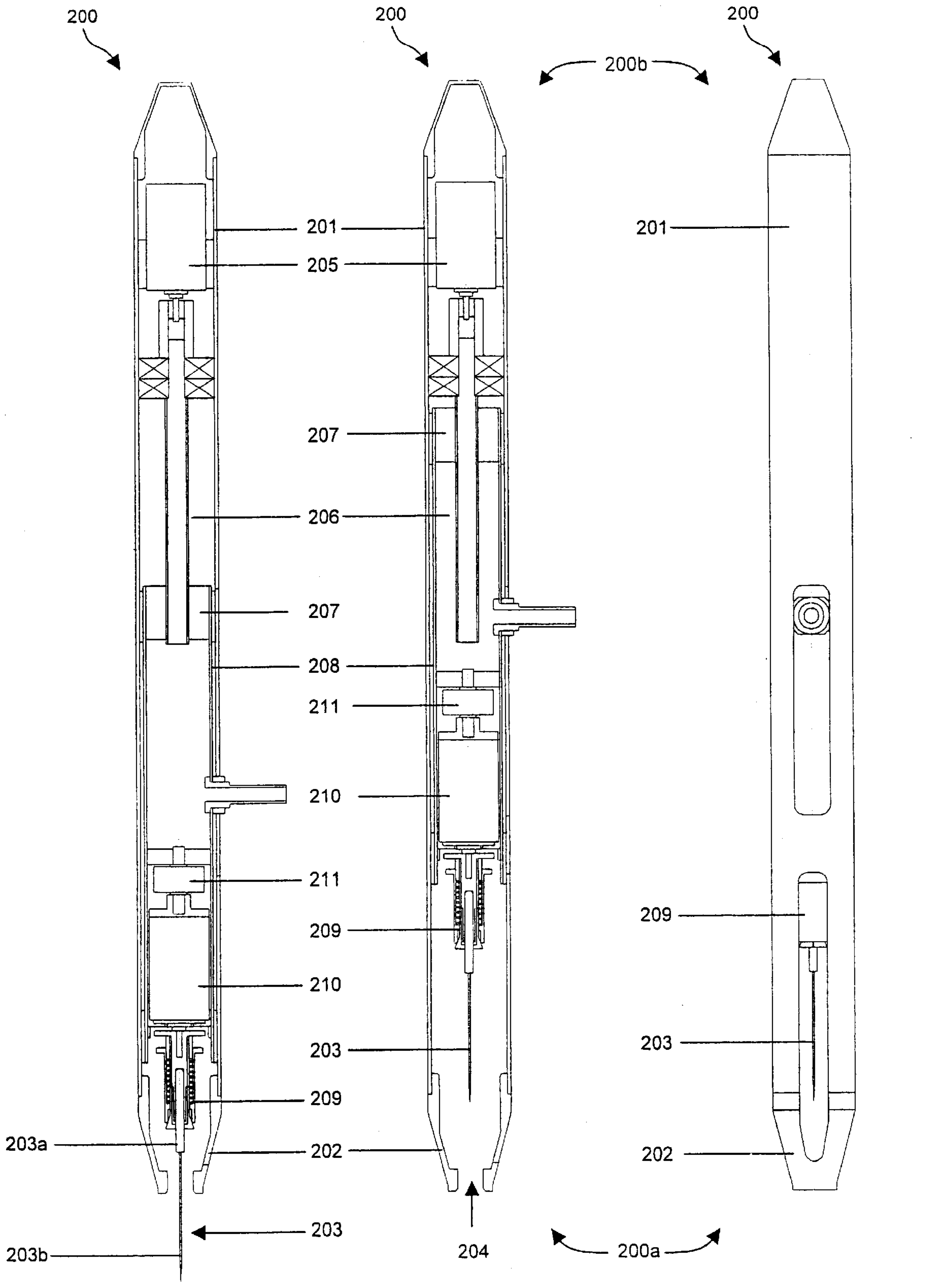
FIGS. 2A–2C show a robotic embodiment of the invention, representing a more complex embodiment of the invention.
Figure 3:
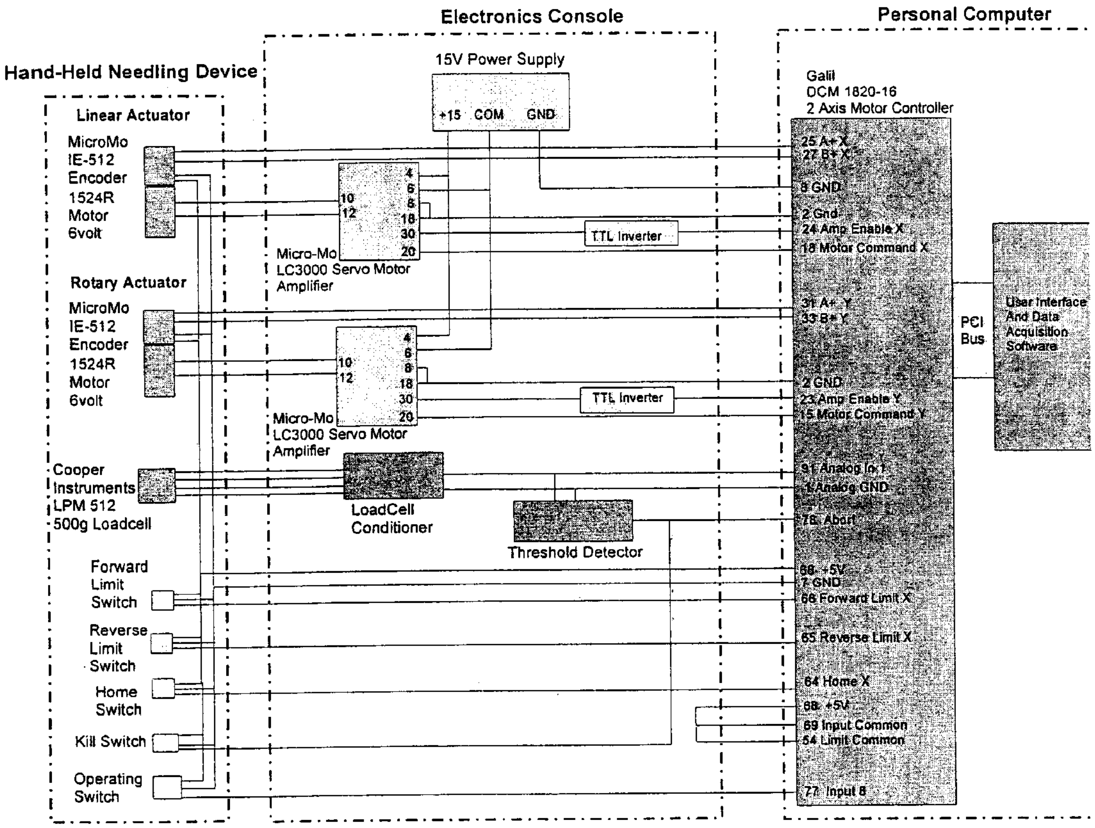
FIG. 3 shows an schematic layout of the embodiment of the invention shown in FIGS. 2A–2C.

At the other end of the spectrum of complexity, FIG. 2 shows a highly complex embodiment, and FIG. 3 schematically illustrates the electrical layout of this embodiment of the invention. This needling instrument 200 is preferably about 20 mm in diameter and about 200 mm long. At this size, the instrument is a convenient hand-held device that is relatively light-weight and easy to use. However, one of skill in the art will understand that the device can be constructed to be significantly larger or smaller without loss of functionality. The device can be viewed as having a proximal end 200*a*, which contacts the subject during operation, and a distal end 200*b*, which is farthest from the subject during operation.

The mechanical components are preferably housed in or otherwise mounted to an encasement 201. The encasement is preferably elongate in character (i.e., of extended length in relation to the transverse dimension of the encasement, having a ratio of length to width which is greater than 1). In a preferred embodiment, the encasement is substantially tubular in structure. In the preferred embodiment, the encasement 201 is made from stainless steel or another durable material which is readily sterilized using heat, steam or chemical sterilization techniques known in the art.

The proximal end of the needling instrument of the invention preferably comprises an extension or "contacting foot" 202 at its proximal end 200*a* designed to rest against the subject during a needling procedure. This extension serves as a means for stabilizing the instrument during needle insertion, manipulation and withdrawal. The needling instrument is constructed to advance the needle 203 (e.g., an acupuncture needle with a handle 203*a* and a needle shaft 203*b* or other needle used for therapeutic needling techniques) through an opening 204, such as a gap or a hole in the foot 202 and into a subject.

In operation, the instrument 200 is centered on a target point, such as an acupuncture point, and held with the foot 202 against the skin. The instrument 200 is then activated to initiate insertion, manipulation (if desired) and pullout of the needle 203. This process is preferably controlled by a computer processor (see the personal computer in FIG. 3) programmed to control the parameters of insertion, manipulation and pullout. Manipulation of the needle involves, for example, uni- or bi-directional rotation, pistoning and/or vibration of the needle. The instrument may also be configured to measure outcomes, such as various physical and/or electrical characteristics of insertion, manipulation and pullout, such as insertion force, torque, and pullout force. All motion parameters, such as depth of needle insertion, rotation distance and speed, and dwell time can be independently programmed.

Advancement and retraction (i.e., needle insertion and pullout) of the needle is driven by a linear actuator. The linear actuator may be any device which can drive linear motion. The linear actuator may, as shown in FIGS. 2 and 3, comprise a motor 205 (referred to herein as a "linear actuating motor"). In a preferred embodiment, the linear actuating motor 205 is a miniature DC servomotor. The linear actuating motor 205 drives advancement and retraction of the needle by a mechanism that translates rotational motion into linear motion. A variety of such mechanisms are known in the art; examples include the use of cam devices, rack and pinion devices, belt and pulley devices, leadscrew devices, as well as hydraulic and pneumatic devices, such as hydraulic and pneumatic cylinders.

In the embodiment shown in FIG. 2, the mechanism for converting the rotational motion of the linear actuating motor 205 into linear motion includes a lead screw mechanism. The linear actuating motor 205 is mounted in the distal portion of the encasement and configured to rotate a ball lead screw 206. The lead screw comprises a nut 207 mounted to tube 208 which extends lengthwise within the encasement 201 in a manner which permits the tube to slide within the encasement 201. Engaging the linear actuator motor 205 generates rotates the ball lead screw within the nut, imparting linear motion of the sliding tube 208 within the encasement 201, which results in linear motion of the needle mount 209, which is mounted either directly or indirectly to the sliding tube 208. This movement is responsible for driving needle insertion and pullout. FIG. 2A shows the needle mount 209 and needle 203 in an extended position. FIG. 2B shows needle mount 209 and needle 203 in a retracted position. This movement is also useful to effect pistoning of the needle in the subject. Engagement of the linear actuator is readily controlled by the computer processor.

Rotation of the needle 203 is effected using a rotational actuator. The rotational actuator may, as shown in FIGS. 2 and 3, comprise a motor 210. In one embodiment of the invention, the linear actuator and the rotary actuator together comprise a single motor. In a preferred embodiment, shown in FIG. 2, rotation is controlled by a separate motor referred to as the "rotary actuator motor" 210, which permits uni- or bi-directional needle manipulation. This motor 210 is suitably a miniature DC servomotor. The rotary actuator motor 210 is suitably mounted at a proximal end of the sliding tube 208, preferably within the sliding tube 208. The needle mount 209 may be mounted, either directly or indirectly, to the shaft of the motor 210. It will be appreciated by one of skill in the art that the needle mount 209 need not be mounted directly to the shaft of the motor 210 and that a variety of gearing mechanisms are possible which would permit the motor 210 to be located in a position in which the shaft is not directly aligned with the needle mount 209.

The motors (when present) are preferably configured as servomotors such that their speeds, directions, and distances of travel can be accurately controlled by computer using closed-loop control system(s). Alternatively, the motors (when present) may be configured as stepper motors such that their speeds, directions, and distances of travel can be accurately controlled by computer using open-loop control system(s).

A linear variable displacement transducer (LVDT) (not shown) may also be incorporated in the needling instrument to provide an absolute measure of axial needle position. The LVDT is useful for establishing the starting position prior to needle insertion and also as a safety check on the needle insertion control system.

The system also preferably comprises a mechanism for measuring push and/or pull force exerted on the needle during operation. A variety of suitable devices are known in the art, for example, miniature compression load cells, miniature tension load cells, miniature tension/compression load cells, and miniature hollow-type load cells. See www.danaloadcell.com and www.cooperinstruments.com. In a preferred embodiment, a uniaxial strain gauge loadcell 211 is configured to measure the axial load applied to the needle, preferably during both needle insertion and needle pullout. Such transducers are extremely reliable and are commercially available in the preferred size and load range (about 450–550 g, preferably 500 g). The maximum force measured by this loadcell 211 during needle pullout (i.e., pullout force) is a primary measurement of needle grasp, discussed above. The miniature uniaxial loadcell 211 is suitably interposed between the rotary actuator motor 210 and the sliding tube 208 to detect loads are communicated through the needle mount 209 and the rotary actuator motor 210. A flexure, may be employed to reject all inadvertent side loads placed on the needle or needle mount. The maximum load recorded by the loadcell 211 during needle pullout is a primary measurement of pullout force. However, more complex curves representing the changes in load during pullout may also be recorded and used as a measure of pullout force. The loadcell 211 may also be used to measure loads occurring during needle insertion.

The torque exerted on the needle during needle manipulation may be suitably measured indirectly by measuring the current of the rotary actuator motor. The motor current may be measured by detecting the voltage drop across a resistor in series with the motor. This current is proportional to the torque delivered by the motor. In an alternative embodiment, the loadcell 211 may be used to detect torque as well as axial load. Additionally, the devices discussed above for measuring mechanical force, or power, transmitted by a rotating shaft, may be incorporated into the instrument, e.g., coupled between the needle mount and the motor shaft, to measure the torque of the needle as it is manipulated by the operator.

The force measured by the loadcell 211 during needle insertion is useful for making a determination of initial needle penetration into the skin. During insertion, the needle initially will be entirely outside of the skin, and the loadcell 211 will measure zero load. As the needle 203 is advanced, the zero insertion reference point is established as the point at which the loadcell 211 first detects axial compressive load, that is, when the needle 203 first begins to encounter resistance to penetration. The needle 203 can then continue to be advanced until a specified stopping point, e.g., until the target depth is reached or until muscle is detected.

The needling instrument of the invention suitably comprises a switch (e.g., a push-button switch), preferably mounted to the encasement 201 of the needling instrument of the invention such that it may easily be activated by the operator. The switch may be configured such that activation instructs the data acquisition system to zero the loadcell 211 in its current position and to begin sampling data. Zeroing the loadcell 211 is useful because the weight of the loadcell 211 itself is significant in comparison to the expected pullout force. Thus, it is preferably zeroed while in the same orientation it will be in while measuring the pullout force. The instrument is suitably configured such that activating the same switch a second time will initiate the needling procedure.

The skin-contacting foot of the needling instrument may also suitably incorporate a loadsensor, e.g., based on a conductive rubber element. This loadsensor is suitably configured to detect the amount of force with which the needling instrument is being held against the subject's skin. Real-time feedback from this sensor is useful for ensuring consistent needling technique. When used as a research tool, this loadsensor can be used to ensure that repeatable conditions are maintained across all test points.

The needle is held in the needling instrument of the invention by a needle mount 209, such as a clamping fixture, configured to grip the blunt end 203*a* of a needle 203, such as an acupuncture needle. In a preferred embodiment, the needle mount 209 comprises a quick-release mechanism, such as a collet clamp, to permit quick engagement and release of the needle 203. Moreover, the needle mount 209 is preferably configured to accept standard disposable acupuncture needles of a variety of lengths.

In one aspect of the invention, the clamping fixture is configured to establish electrical continuity with the needle such that EMG signals may be detected using the acupuncture needle as the EMG probe. A switch (not shown) may be provided to break this circuit at all times except when EMG signals are being collected. Breaking the circuit will eliminate the possibility of any small electric current passing through the EMG amplifier from interfering with the normal behavior of the tissues at target points.

In a preferred embodiment for research use, EMG signals are detected and amplified using a Cadwell 6200A EMG unit with its bandpass filters set to 10–10,000 Hz. The EMG signal may be fed to an analog power meter, the output of which varies from zero to a predetermined maximum as an indication of the power level of the EMG signal. This signal can, for example, be used to detect the presence or absence of injury potentials indicating penetration of skeletal muscle by the needle 203. Moving a needle through connective tissue produces an EMG signal of a very low power level. On penetrating muscle, the power level spikes to approximately 10 times its baseline level. This spike is easily detected.

In a preferred embodiment, a personal computer is fitted with digital-to-analog and analog-to-digital converters to control the needling instrument and/or to collect data. A customized software system has been written using the LABVIEW software package (National Instruments, Austin, Tex.). This system performs three primary functions. First, it controls the servomotors in the needling instrument by sending the appropriate analog command signals to the motors. Second, it records and saves data (loadcell, torque, motor position, LVDT and EMG signals). Third, it performs randomizations associated with the needling procedures for research purposes. The software is suitably programmed to instruct the needling device to reproduce any of a wide variety of needling techniques, such as insertion, pistoning, uni- and bi-directional rotation, and pullout. Additionally, the system may be programmed to accept, record and manipulate data from the needling instrument relating to the physical characteristics of the interaction of the needle with the tissue. Additionally, the recorded physical characteristics may be used to determine whether a needling technique has successfully achieved a therapeutically acceptable degree of needle grasp, and may provide such data as feedback to the operator or may use such data to control the operation of the instrument. For example, the system may simply notify the operator that needle grasp was not achieved and instruct the operator to move the device to another location. As another example, the system may continue to manipulate the data for a predetermined period or until adequate torque is sensed to indicate that needle grasp has occurred.

The in vivo use of any electromechanical instrument raises the concern of patient safety. Use of the needling instrument has two potential sources of risk: mechanical and electrical. The exemplified embodiment shown in FIGS. 2A–2C has design features which minimize or eliminate such risks. The computer control system is programmed to continuously monitor parameters of the needle insertion, such as the depth of needle insertion and the force of insertion/pullout. If any of these parameters exceeds a predetermined safe range, the system will automatically stop operation of the needling device. Preferred thresholds are as follows: 1) LVDT detecting that the needle is being inserted 2 mm deeper than the target depth; and 2) maximum insertion or pullout force reaching 3.9N.

The axial travel of the needle 203 (i.e., insertion) is preferably also limited by a mechanical stop. For example, in one embodiment the travel of the needle is limited by the mechanical contact of the needle mount 209 with the foot 202.

Where motors, such as servomotors, are used in the instrument, they are preferably very small, low power motors, not capable of delivering substantially higher force/torque than is useful for normal operation of the instrument. If unusually high resistance is encountered in the tissue, the motors will simply stall. The stall torque of the needle rotation motor is preferably about 1.5 mNm. This is considered to be a safe torque and is substantially less than the torque required to plastically deform the needle (22 mNm), or the torque required to separate the needle shaft from its handle (39 mNm). The insertion/retraction motor will stall if either the insertion or pullout force exceeds approximately 4.9N (equivalent to the weight of a 500 g mass). This is substantially lower than the quality control load of 13.7 N used by the needle manufacturer to ensure needle integrity.

A kill switch is preferably mounted on the body of the needling instrument such that its operation can be halted by the operator instantaneously if a problem is detected. In the exemplified embodiment, the kill switch is mounted on the needling instrument and is configured to instantaneously disconnect all sources of electrical power.

In a preferred embodiment, all components of the system, with two exceptions, are powered by low voltage batteries (e.g., less than 9 Volts). This design greatly reduces the electrical risk, since there is no physical connection to high voltage wall current. One of the two components that derive power from wall current is the electronics unit that conditions the LVDT and the strain gauge load cell. This electronics unit is preferably powered by medical grade isolated power supplies. The connections between this unit and the sensors mounted on the needling instrument are further isolated by optical isolation amplifiers. The other component powered by wall current is the Cadwell EMG amplifier, a commercial machine, which fully incorporates medical grade electrical isolation. All electrical connections between needling instrument (which contacts the patient) and the rest of the control and data acquisition system will preferably incorporate optical isolation amplifiers.

Needle EMG electrodes inserted into skeletal muscles produce brief bursts of electrical activity which are thought to represent discharges from injured muscle fibers (59). With amplification and audiovisual display of the EMG potentials, it is possible to reliably determine exactly when the needle passes through the peri-muscular fascia into the muscle by observing the presence of this insertional activity. Performing muscle insertion thickness determination after measuring the pullout force will ensure that pullout force measurements are not affected by prior EMG recording.

Figure 4A:
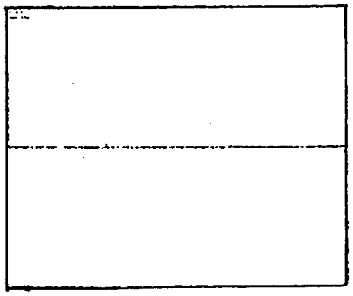
FIG. 4A shows an EMG tracing recorded through an acupuncture needle inserted into subcutaneous tissue only.
Figure 4B:
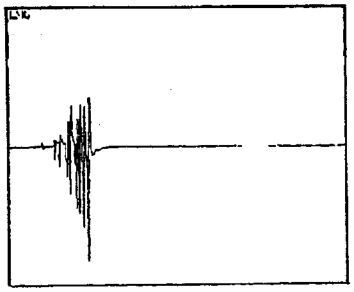
FIG. 4B shows an EMG tracing recorded through an acupuncture needle inserted into muscle tissue, showing insertional activity.
Figure 4C:
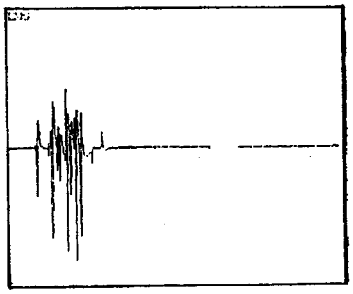
FIG. 4C shows a repeat insertion into muscle at the same location showing that prior muscle penetration by the acupuncture needle does not affect detection of insertional activity.

Preliminary measurements show that prior muscle penetration by an acupuncture needle does not affect detection of the insertional activity during subsequent insertions (FIGS. 4A–4C). FIG. 4A shows an EMG tracing recorded through an acupuncture needle inserted into subcutaneous tissue only. FIG. 4B shows an EMG tracing recorded through an acupuncture needle inserted into muscle tissue, showing insertional activity. FIG. 4B shows a repeat insertion into muscle at the same location showing that prior muscle penetration by the acupuncture needle does not affect detection of insertional activity.

As noted above, the system is suitably configured such that activating a push-button switch instructs the data acquisition system to zero the loadcell 207 and begin sampling data from the loadcell 207 and LVDT sensors; furthermore, activating the switch a second time will initiate the needling procedure. In operation, the operator simply needs to hold the needling instrument steady against the skin while the needle is automatically inserted and manipulated. Where longer dwell times (e.g., time between needle insertion and pullout or time between needle manipulation and pullout) are desired, the needling instrument can be disconnected from the needle while the dwell time elapses. During this period, other points can be tested. The needling instrument can later be reattached to the original needle(s), and the pullout portion of the needling procedure carried out. In a preferred embodiment, the computer is programmed to track the elapsed dwell time and to prompt the investigator to return to previously inserted needles at the appropriate times. Suitable dwell times generally range from about 10 seconds to about 30 minutes or more.

During the pullout phase of each needling procedure, the data acquisition system will preferably monitor the load detected by the loadcell 211. The maximum load encountered during pullout can be used as an indicator of the pullout force for that point. The data acquisition system preferably will identify and save this value automatically without intervention by the investigator. For research purposes, the investigator will not know the value of any of the pullout forces until the completion of the entire test protocol.

Rotary torque is evaluated, for example, by measuring the current passing through the rotary actuator motor during needle rotation. Ideally, this current is proportional to the torque developed by the motor. There are several confounding factors such as motor friction, and torque due to accelerations, but the majority of the torque generated is communicated directly to the needle. The motor current may be detected by measuring the voltage drop across a resistor in series with the motor.

The electronics console suitably comprises current amplifiers for both servomotors, the signal conditioner for the load cell, and circuitry to detect fault conditions such as overloads on the loadcell 207. The computer contains a motor controller which drives the motion of both actuator motors under closed loop control. Data collection is also suitably performed by the motor controller.

The needling device of the invention is preferably configured to use commercially available sterile disposable stainless steel acupuncture needles, 30 to 50 mm in length and 0.25 mm in diameter (32 gauge). The needling device is preferably configured to automatically perform all needling procedures (insertion, manipulation, and pullout), and is preferably computer-controlled so that all needling parameters can be programmed. Needling parameters generally include speed of insertion, depth of insertion, speed of rotation, direction of rotation, amount of rotation, and speed of pullout.

The invention thus provides a needling instrument which can be programmed to execute the specific motions in a manner consistent with conventional acupuncture practice as well as more modem needling techniques.

It will be appreciated that the needling device can be readily modified to replicate other needle manipulation techniques, such as pistoning of the needle and/or vibration of the needle.

Research Methods

In one aspect of the invention, the needling device of the invention is used to examine the effect of needling parameters on the physical characteristics of the interaction of the needle with the tissue of the subject, such as pullout force and rotation torque. In this aspect, the needling device is preferably configured to be controlled by a computer, as described in more detail above, to perform needle insertion, manipulation and pullout maneuvers. The use of the needling device of the invention will eliminate sources of variability and bias in the investigation of such needling techniques. Examples of primary outcome measures include pullout force (e.g., measured as the peak force required to pull an acupuncture needle out of the tissue) and rotation torque. However, other quantitative measures of the needle grasp phenomenon can be used alternatively, or in addition to, pullout force. Examples of parameters that may be suitably controlled by the computer controlled needling device of the invention include dwell time, procedure type (e.g., insertion only, insertion followed by unidirectional rotation and insertion followed by bidirectional rotation). Additionally, the device can be used to measure muscle insertion thickness, e.g., by electromyographic recording of muscle insertional activity during a repeated insertion of the same total depth after measurement of the pullout force. The computer is also suitably programmed to permit input of other variables, such as subjective rating of sensations experienced by the subject during insertion and manipulation of the needle, e.g., using a numerical graphic rating scale.

Our preliminary measurements are consistent with a conclusion that the needle grasp component of de qi is of greater magnitude at acupuncture points than at control points. Needle grasp is potentially a measurable physiological link between tissue cellular events and the network of acupuncture points described in Chinese medicine. Investigation of the mechanism underlying needle grasp is therefore important to advance a scientific understanding of the practice of acupuncture and an understanding of acupuncture's theoretical framework. This information will be applicable to a wide range of different acupuncture styles, theories and methods.

Therapeutic Methods

The needling instrument of the invention is useful for performing needling procedures using any combination of parameters. As an example, needling instrument can execute a standard needle insertion followed by bidirectional manipulation and pullout as follows:

1. Insert needle to a depth of 2 cm at a rate of 1 cm/second
2. Pause for 3 seconds
3. Rotate the needle clockwise 180 degrees at a rate of 4 revolutions/second
4. Rotate the needle counterclockwise 180 degrees at a rate of 4 revolutions/second
5. Repeat the previous two rotation steps 8 times
6. Pause for 3 seconds
7. Execute needle pullout at a rate of 2 cm/second When used in a therapeutic environment, the needling device of the invention permits highly controlled needling technique, which can be optimized for specific therapeutic contexts and/or for specific needling points, to produce optimal therapeutic effect. The needling device of the invention can, for example, precisely control insertion speed and depth, can control the time and torque of unidirectional or bidirectional rotation, and can control the pullout speed and force.

Measurements such as pullout force and torque may be used to determine whether a therapeutically effective degree of needle grasp has been achieved. Moreover, the system may be configured to cause the needle to rotate until a predetermined torque has been achieved, thereby ensuring a therapeutic degree of needle grasp. In a complex embodiment of the invention, the satisfaction of a predetermined pullout force or torque may be communicated to the operator by any a wide variety of computer output means. In a less complex embodiment, the needling device may be configured to make a sound, provide a visual output, such as activation of a light, or provide any other manner of sensory output to alert the user to the satisfaction of the predetermined requirement.

As an example, the insertion speed can be set at 1–2 cm per second, other parameters can be set as described in Chiang et al (19), e.g., for bidirectional rotation, and the same parameters without reversal of direction for unidirectional rotation.

Diagnostic Methods

The needling instrument of the invention opens the door to an entirely new family of diagnostic methods. The needling instrument provides a means for evaluating characteristics of human tissue, most especially fascia and other connective tissue.

For example, the needling device has the capacity to be used in diagnostic methods for a variety of musculoskeletal conditions, such as myofascial pain syndrome (MPS), for which there is currently no objective diagnostic test. MPS is an extremely common diagnostic entity among patients suffering from chronic musculoskeletal pain. MPS is reported to be present in 85% of patients admitted to a chronic pain center, and 10% of patients presenting to primary care clinics. MPS is probably a heterogeneous group of conditions, all of which produce similar symptoms. Because there is currently no objective diagnostic test to evaluate patients suspected of having MPS, this frequent diagnosis is therefore currently made totally on the basis of physical exam findings: physicians palpate the skin and underlying tissues, feeling for localized tender areas of connective tissue and muscle tissue that subjectively feel firm, thickened, and less mobile. This palpation method is subjective, and has been demonstrated to be unreliable, with poor inter-observer agreement. The treatment of MPS is at present empiric, with massage, ultrasound, pharmacologic agents, exercise, "stretch and spray" technique, injection of local anesthetics, as well as simple "dry needling", a technique similar to acupuncture. Clinical trials attempting to evaluate these forms of treatment to date have all relied on physical examination to make the diagnosis of myofascial pain syndrome, which puts into question any conclusion derived from these trials. A method to objectively identify tissue abnormalities associated with MPS will therefore be important, from the point of view of both research and clinical practice, by improving physicians' ability to diagnose MPS, and allowing clinical trials to evaluate therapies for a large proportion of patients with chronic pain.

The method disclosed here entails inserting a small diameter needle (e.g., a 0.25 mm diameter acupuncture needle) through the skin and into the underlying connective tissue and muscle. The needle is then mechanically manipulated by either rotating it, or pistoning it longitudinally. This manipulation causes the tissue to adhere to the needle to varying degrees. The adherence is believed to be largely due to connective tissue fibers becoming entwined around the needle. The more the tissue winds around the needle, the more it grips the needle. The magnitude of this gripping can subsequently be evaluated either by measuring the torque required to continue rotating the needle (rotation torque), or by measuring the amount of force required to pull the needle out of the tissue (pullout force). Musculoskeletal conditions such as MPS may be associated with abnormal connective tissue thickness, mobility, stiffness and amount of adherence to muscle, which would be consistent with findings found on physical examination. These biomechanical abnormalities may be detectable using the diagnostic method of the invention, by measuring abnormal levels of torque or pullout force. Measurement of torque/pullout force may therefore allow the objective measurement of apathological change in tissues in MPS.

EXAMPLES

Comparison of Pullout Force at Acupuncture Points vs. Control Points

Figure 5:
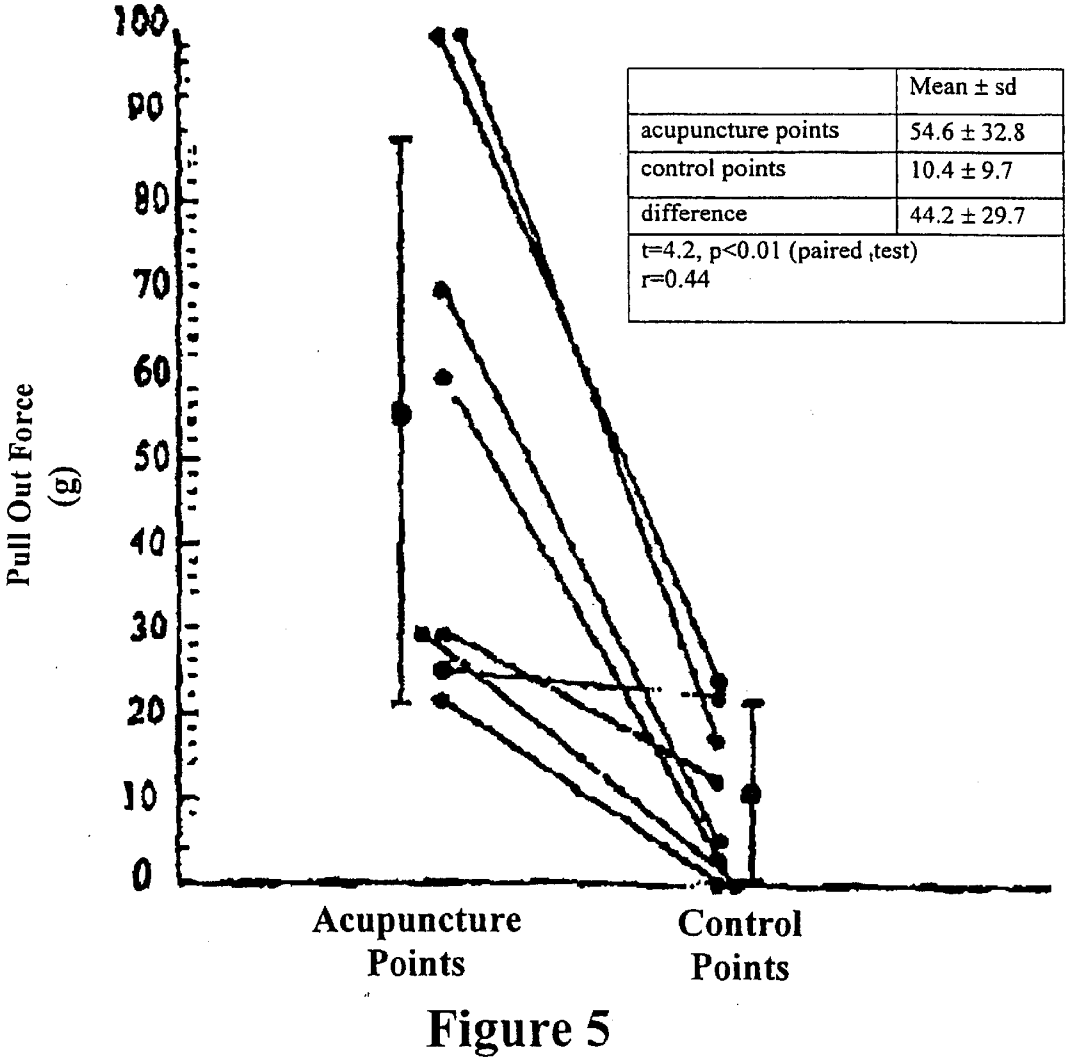
FIG. 5 shows a comparison of pullout force measured one minute after needle insertion and pullout force following manipulation (unidirectional rotation for 2 seconds) in acupuncture and control points.

An estimate of the pullout force was obtained using a spring scale device shown in FIG. 1A in eight individuals. Each individual was needled at acupuncture point Quchi (L.I. 11) and at one control point on the contralateral arm 1 cm proximal to the contralateral Quchi. (Quchi is located approximately halfway between the lateral epicondyle of the humerus and the lateral end of the elbow crease.) Depth of needle insertion was approximately 1 cm. FIG. 5 shows the pullout force measured one minute after needle insertion and manipulation (unidirectional rotation for 2 seconds) in both acupuncture and control points. There was a significant difference in pullout force between the acupuncture and control points. The mean pullout force was 54.6 g±32.8 g at acupuncture points and 10.4±9.7 g at control points, with a difference between paired values of 44.2±29.7 g. Paired t test: t=4.2, p<0.01. Within subject correlation between acupuncture and control points: r=0.44.

Pullout Force of Needles Inserted into Subcutaneous Tissue Only, with and Without Manipulation Preliminary measurements were conducted to verify that high pullout forces induced by needle manipulation can be detected in the likely absence of muscle penetration. The pullout force was measured ten seconds after insertion at acupuncture point Baohuang (U.B. 53) bilaterally (located on the lower back lateral to the sacrum). Six individuals were tested. For all insertions, needle depth was half of the skin bifold thickness minus 0.5 cm. It is therefore unlikely that the needle penetrated into muscle tissue. If muscle penetration did occur, it was small in comparison to the depth of subcutaneous tissue penetration. On one side of the body (randomly assigned), the needle was inserted and manipulated by unilateral rotation for 2 seconds. On the contralateral side, the second needle was inserted without manipulation (FIG. 4). The mean pullout force was 58.1 g±42.3 g with insertion and unidirectional rotation compared with 5.3 g±4.6 g with insertion only. This difference was statistically significant. Paired t test t=2.57, p<0.05. This result is consistent with a conclusion that needle manipulation has an effect on the pullout force and that this effect can be demonstrated with small or absent muscle penetration.

Use of EMG to Determine Degree of Muscle Penetration

Studies were performed to determine whether EMG insertional activity can be recorded through an inserted acupuncture needle connected to an EMG cable (see FIGS. 4A–4C). Results were positive and repeat EMG recordings at the same point showed that prior muscle penetration by the acupuncture needle does not affect detection of insertional activity during subsequent needling. FIG. 3*a* shows an EMG tracing recorded through an acupuncture needle inserted into subcutaneous tissue only. FIG. 3*b* shows an EMG tracing recorded through an acupuncture needle inserted into muscle tissue, showing insertional activity. FIG. 3*c* shows a repeat insertion into muscle at the same location showing that prior muscle penetration by the acupuncture needle does not affect detection of insertional activity.

Preliminary Data Obtained Using Needling Instrument of the Invention

A study is currently underway in which the pullout force at 8 acupuncture points (AP) and 8 corresponding contralateral control points (CP) in 80 normal human subjects is being measured. A novel and important aspect of this study is that all acupuncture needles are inserted, manipulated and pulled out using the computer-controlled mechanical instrument shown in FIG. 2. Pullout force is measured automatically by the instrument as the needle is pulled out of the skin, ensuring controlled experimental conditions and eliminating sources of investigator bias. The needle movement parameters (insertion speed, rotation speed, rotation angle, pullout speed) were chosen to be consistent with acupuncture practice. At each point, needle insertion depth is set in proportion to subcutaneous tissue thickness as determined by ultrasound. The same depth is used for corresponding acupuncture and control points.

A secondary research question addressed in this study is whether the method of needle manipulation influences needle grasp. Subjects are randomized to one of three manipulation types: needle insertion only with no manipulation (NO), needle insertion followed by either bi-directional rotation (BI), or uni-directional rotation (UNI).

The acupuncture vs. control comparison is made within subjects, with acupuncture and control points randomized to right and left sides of the body. Control points are located within a 2 or 3 cm radius (depending on location) of the contralateral acupuncture point. Subjects are blind to both procedure type and acupuncture vs. control variables.

Figure 6A:
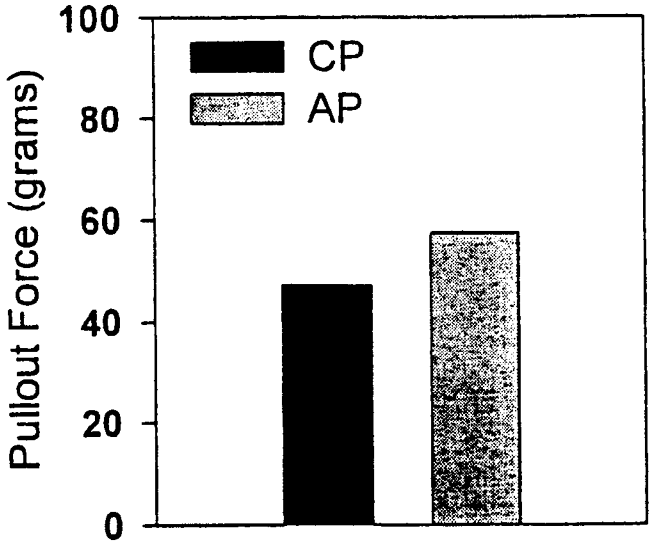
FIGS. 6A and 6B show preliminary results comparing pullout force at acupuncture points and corresponding control points (FIG. 6A), and comparing pullout force resulting from three different needling procedure types (FIG. 6B).
Figure 6B:
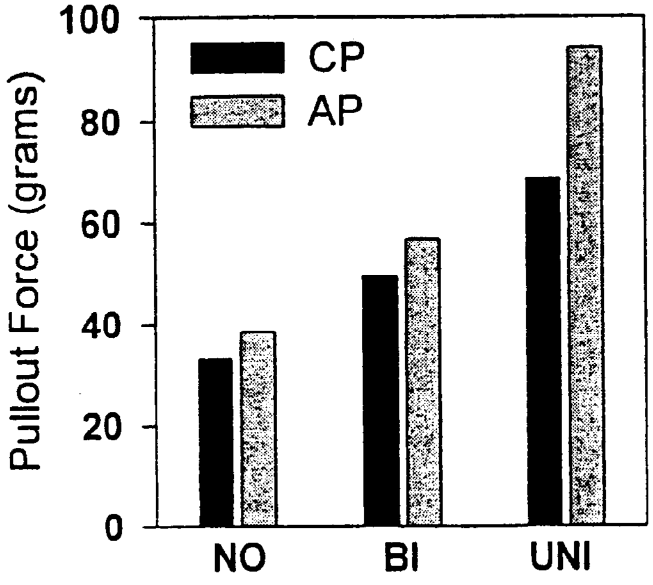

Results from the first 33 subjects show that pullout force at acupuncture points is 22% higher than at corresponding control points (57.5 g vs. 47.1 g) (FIG. 6A). This difference is statistically significant (repeated measures ANOVA, p<0.001). There is also a significant difference in pullout force between the three needling procedure types (p<0.001) (FIG. 6B). This difference is significant both at acupuncture points and at control points.

These results provide objective evidence that acupuncture points have different biomechanical behavior than control points. Accordingly, one aspect of the invention is the identification of acupuncture points in populations and/or in individuals by measuring pullout force. These results also show that needle manipulation strongly influences needle grasp at control points as well as at acupuncture points.

REFERENCES

Various references have been cited throughout the specification. The entire disclosure of each such reference (including, without limitation, the following) is incorporated herein.

1. The Academy of Traditional Chinese Medicine. An outline of Chinese acupuncture. Beijing: Foreign Language Press, 1975: 6–16.
1a. Ibid.: 95–216.
2. Ibid.: 226–299.
2a. Angell M, Kassirer J P. Alternative Medicine—The risks of untested and unregulated remedies. N Engl J Med 1998; 339:839–841.
3. Austin M. Acupuncture therapy. New York: ASI Publishing, 1972.
4. Baldry P E. Acupuncture, trigger points and musculoskeletal pain. Edinburgh: Churchill Livingstone, 1989.
5. Becker R O, Marino A A. Electromagnetism and life. Albany: State University of New York Press, 1982.
6. Beijing, Shanghai and Nanjing Colleges of Traditional Chinese Medicine. Essentials of Chinese Acupuncture. Beijing: Foreign Language Press, 1980:105–297.
7. Ibid.: 307–310.
8. Ibid.: 322–396.
8a. Ibid.: 6–7.
9. Blanchard B M. Deep vein thrombophlebitis after acupuncture. Ann Int Med 1991;115:748.
10. Bloom and Fawcett. A textbook of histology. Chapman and Hall, 1994.
11. Bossy J et al., Substratum macroscopique des points d'acupuncture. Bulletin de l'Association Anatomique 1975; 49:357–362.
12. Bossy J. Morphological data concerning the acupuncture points and channel network. Acup and ElectroTherap Res Int J 1984; 9:79–106.
13. Burdon D W. Acupuncture needles as a cause of bacterial endocarditis. Br Med J 1983; 287: 6.
14. Cassidy C A. A survey of six acupuncture clinics: demographic and satisfaction data. In: Proceeding of the third symposium of the society for acupuncture research. Georgetown University Medical Center, September 1995: 1–27.
14a. Chapman C R, Benedetti C, Colpitts Y H, Gerlach R. Naloxone fails to reverse pain thresholds elevated by acupuncture: acupuncture analgesia reconsidered. Pain 1983; 16:13–31.

14b. Chen B M, Grinnell A D. Kinetics, calcium dependence and biophysical properties of integrin-mediated mechanical modulation of transmitter release from frog motor nerve terminals. J Neurosci 1997; 17:904–916.
14c. Chen C S, Mrksich M, Huang S, Whitesides G M, Ingber D E. Geometric control of cell life and death. Science 1997;276:1425–1428.
15. Cheng Xinnong. Chinese acupuncture and moxibustion. Beijing: Foreign Language Press, 1987:1–10.
16. Ibid.: 111.
17. Ibid.: 108–243.
18. Ibid.: 325–326.
18a. Ibid.: 272.
19. Chiang Ching-Tsai, Chin Hsin-Ling, Yang Lian-Fang. Peripheral afferent pathways for acupuncture analgesia, *Scientia Sinica* 1973;16: 210–217.
19a. Chicurel M E, Chen C S, Ingber D E. Cellular control lies in the balance of forces. Current Opinion in Cell Biology 1998;10:232–239.
19b. Chicurel Me, Singer R H, Meyer C J, Ingber D E. Integrin binding and mechanical tension induce movement of mRNA and ribosomes to focal adhesions. Nature 1998;392:730–733.
19c. Chiquet M, Matthisson M, Koch M, Tannheimer M, Chiquet-Ehrismann R. Regulation of extracellular matrix synthesis by mechanical stress. Biochem. Cell Biol.1996;74:737–744.
20. Chu L S W, Yes S D J, Wood D D. Acupuncture manual: a western approach. New York: Marcel Dekker, 1979: 24–27.
20a. Ibid.:84–113.
20b. Ciczek M, Szopinski J, Skrzypulec V. Investigations of morphological structure of acupuncture points and meridians. J Trad Chin Med 1985; 5:289–292.
21. Comunetti A, Laage S, Schiessl N, Kistler A. Characterization of human skin conductance at acupuncture points. Experientia 1995; 51:328–331.
21a. Condic M L, Letoumeau P C. Ligand-induced changes in integrin expression regulate neuronal adhesion and neurite outgrowth. Nature 1997;389:852–856.
22. Croley T E and Carlson M. Histology of the acupuncture point. Am J of Acup 1991; 19:247–253
22a. The Council for Scientific Medicine. A statement in defense of scientific medicine. Sci Rev Alt Med 1997; 1:2–3.
23. Denmei S. Introduction to meridian therapy: classical Japanese acupuncture. Seattle: Eastland Press, 1990: 168–182. [Originally published as *Kei Raku Chiryo no Susume.*]
23a. Dike L A, Ingber D E. Integrin-dependent induction of early growth response genes in capillary endothelial cells. J. Cell Science 1996;109:2855–2863.
24. Dray A. Neuropharmacological mechanisms of capsaicin and related substances, Biochem Pharmacol 1992; 44:611–615.
25. Dung H C. Anatomical features which contribute to the formation of acupuncture points, Am J Acupuncture 1984;12:139–144.
26. Dung H C. Acupuncture points of the cranial nerves. Am J Chin Med 1984;12:80–92.
27. Dung H C. Acupuncture points of the cervical plexus. Am J Chin Med 1984; 12:94–105.
28. Dung H C. Acupuncture points of the typical spinal nerves. Am J Chin Med 1985;13:39–47.
29. Dung H C. Acupuncture points of the lumbar plexus. Am J Chin Med 1985;13:133–143.
30. Dung H C. Acupuncture points of the sacral plexus. Am J Chin Med 1985;13:145–156.
31. Dung H C. Acupuncture points of the brachial plexus. Am J Chin Med 1985;13:49–64.
32. Eisenberg D M, Kessler R C, Foster C, Norlock F E, Calkins D R and Delbanco T L. Unconventional medicine in the United States. N Engl J Med 1993; 328:246–252.
33. Ellis A, Wiseman N, Boss K. Fundamentals of Chinese acupuncture. Brookline: Paradigm Publications, 1991.
39. Garcia A A, Venkatarama A. Bilateral psoas abscesses following acupuncture. West J Med 1994;161:90.
40. Gilberg J G. Auricular complication of acupuncture. NZ Med J 1987;100:141–2.
41. Goldberg B, Rabinovitch M. Connective tissue. In: Weiss L. Cell and tissue biology. Urban and Schwarzenberg, 1988.
41a. Grevert P, Goldstein A. Placebo analgesia, naloxone, and the role of endogenous opioids. In:White L, Tursky B, Schwartz G E, eds. Placebo: theory, research and mechanisms. New York: Guilford Press, 1985: 332–350.
42. Gunn C C. Type IV acupuncture points. Am J Acup 1977; 5(1):51–52.
43. Gunn C C. Treating myofascial pain. Seattle: University of Washington, 1989.
44. Gunn C C, Milbrandt W E. The neurological mechanism of needle grasp in acupuncture. Am J Acup 1997; 5:115–120.
44a. Halvorsen T V, Anda S S, Naess A B, Levang O W. Fatal cardiac tamponade after acupuncture through congenital sternal foramen. Lancet 1995; 345:1175.
44b. Hammerschlag R. Methodological and ethical issues in acupuncture research. NIH Consensus Development Conference on Acupuncture (1997) 45–49.
44c. Head H. On the disturbance of sensation with special reference to the pain of visceral disease. Brain 1893; 16:1–133.
45. Heine H. Anatomical structure of acupoints. J Trad Chin Med 1988; 8(3): 207–212.
46. Heine H. The morphological basis of the acupuncture points. Acup 1990;1:1–6.
47. Heine H. Zur Morphologie der Aklupunkturpunkte. Dtsch Zschr Akup 1978;21:75–79.
48. Helms J M. Acupuncture Energetics—A Clinical Approach for Physicians. Berkeley: Medical Acupuncture Publishers, 1995: 22.
49. Ibid.: 281–285.
50. Ibid.: 303–574.
51. Ibid.: 613–643.
52. Hynes R O. Integrins: A family of cell surface receptors. Cell 1987;48:549–554.
52a. Ingber D E. Tensentegrity: the architectural basis of mechanotransduction. Annu Rev Physiol 1997;59:575–599
53. Johns R. The art of acupuncture techniques. Berkeley: North Atlantic Books, 1996.
54. Kaptchuck T J. The web that has no weaver. New York: Congdon & Weed, 1983.
55. Kent G P, Brondum J, Keenlside R A, LaFazia L M, Scott H D. A large outbreak of acupuncture-associated Hepatitis B. Am J Epidemiol 1988; 127:591–198.
55a. Kern A, Marcantonio E E. Role of the I-domain in collagen binding specificity and activation of the integrins 1 1and 2 2. J.Cell.Physiol. 1998;176:634–641.
56. Kida Y et al. Cervical spinal cord injury caused by acupuncture. Arch Neurol 1988; 45: 831.
57. Kim B H. On the Kyungrak System. Pyongyang, 1963.
58. Kimura M et al. Electron microscopical and immunohistochemical studies on the induction of 'qi' employing needling manipulation. Am J Chin Med 1992; 20:25–35.

59. Kugelberg E, Petersen I. "Insertion activity" in electromyography, with notes on denervated muscle response to constant current. J Neurol Neurosurg Psychiatry 1949; 12:268.
60. Lao L. Safety issues in acupuncture. J Alt Compl Med 1996; 2:27–31.
60a. Lao L. Acupuncture techniques and devices. J Alt Compl Med 1996; 2:23–25.
61. Lewith G T, Machin D. On the evaluation of the clinical effects of acupuncture. Pain 1983;16:111–127.
62. Li Xuemei, Zhao Jingyi. Acupuncture patterns and practice. Seattle: Eastland Press, 1993.
63. Liao S J. Acupuncture points: coincidence with motor points of skeletal muscle. Arch Phys Med Rehab 1975; 6:550.
64. Liao S J, Lee H H M, Ng L K Y. Principles and Practice of Contemporary Acupuncture. New York: Marcel Dekker,1994: 8–41.
65. Ibid.: 74–136.
66. Ibid.: 161.
67. Liu Y K. The correspondence between some motor points and acupuncture loci. Am J Chin Med 1975; 3:347–358.
68. Lohman T G, Roche A F, Martorell R. Anthropometric standardization reference manual. Champaign: Human Kinetics Books, 1988: 55–70.
69. Lytle C D. An overview of acupuncture. Center for Devices and Radiological Health, U.S. Department of Health and Human Services, 1993
70. Lytle C D. Safety and regulation of acupuncture needles and other devices. In: NIH Consensus Development Conference on Acupuncture, 1997: 51–53
71. Maciocia G. The practice of Chinese medicine. Edinburgh: Churchill Livingstone, 1994.
72. McCarroll G D, Rowley B A. An investigation of the existence of electrically located acupuncture points. IEEE Trans Biomed Eng 1979; 26:177–182.
73. Melzack R, Stillwell D M, Fox E T. Trigger points and acupuncture points for pain: correlations and implications. Pain 1977;3:3–23.
73a. Muller J M, Chilian W M, Davis M J. Integrin signaling transduces shear stress-dependent vasodilatation of coronary arterioles. Circ Res 1997; 80:32–36.
74. Murray H M, Rubel A J. Physicians and healers, unwitting partners in health care. N Engl J Med 1992; 326:61–64.
74a. Mussat M. Physique de l'acupuncture: hypotheses et approches experimentales. Paris: Librairie la Francois, 1983. Transl. Helms J M.
75. Needham J. Science and civilization in China: Volume 2. Cambridge: Cambridge University Press, 1956.
76. Ng L K Y, Katims J J, Lee M H M. Acupuncture: a neuromodulation technique for pain control. In: Aronoff G M. Evaluation and treatment of chronic pain: 2nd ed. Williams and Wilkins, 1992.
77. Ng L K Y. What is acupuncture? In: NIH Consensus Development Conference on Acupuncture, 1997: 19–23.
78. Niboyet J E H. Nouvelles constatations sur les proprietes electriques des points chinois. Bull Soc D'Acup 1938; 4:30
79. Niboyet J E H, Mery A. Compte rendu de recherches experimentales sur les meridiens chez le vivant et chez le cadavre. Acte des IIIemes Journees Internationales d'Acupuncture 1957; 47–51.
81. NIH Consensus Development Conference on Acupuncture, Nov 1997. Consensus statement.
82. Noordegraaf A, Silage D. Electroacupuncture. IEEE Trans Biomed Eng 1973; 20:364–366.
82a. Pirog J. Practical application of meridian style acupuncture. Berkeley: Pacific View Press, 1996.
83. Rabischong P, Niboyet J E H, Terral C, Senelar R, Casez R. Bases experimentale de l'analgesie acupuncturale. La Nouvelle Presse Medicale 4; 28 (1975) 2021–2026.
84. Reishmanis M, Marino A A, Becker R O. Electrical correlates of acupuncture points. IEEE Trans Biomed Eng 1975; 22:533–535.
85. Richardson P H, Vincent C A. Acupuncture for the treatment of pain: a review of evaluative research. Pain 1986; 24:15–40.
86. Riet G et al., Acupuncture and chronic pain, a criteria based meta analysis. J Clin Epidemiol 1990; 43: 1191–1199.
86a. Riihimaki T. OMS Medical Supplies (Major distributor of acupuncture needles in the United States) Personal communication.
87. Robbins, Pathologic basis of disease. Philadelphia: W. B. Saunders, 1989.
87a. Salter D M, Robb J E, Wright M O. Electrophysiological responses of human bone cells to mechanical stimulation:evidence for specific integrin function in mechanotransduction. J Bone Miner Res 1997; 12:1133–1141.
88. Sandberg L B, Soskel N T, and Lestie J G. Elastin structure, biosynthesis and relation to disease states. N Engl J Med 1981; 304:566–579.
89. Seem M. Bodymind energetics. Rochester: Thorsons Publishers, 1987.
90. Seemayer N B, Soskel N T, Lagace R. Myofibroblasts in human pathology. Human Pathology 1981;12:491–492.
91. Senelar R. Les caracteristiques morphologiques des points chinois. In: Niboyet J E H. Nouveau traite d'acupuncture. Maisonneuve:1979: 249–277.
91a. Shang C. Singular point, organizing center and acupuncture point. Am J Chin Med 1989;17:119–127.
91b. Shang C. Bioelectrochemical oscillations in signal transduction and acupuncture-an emerging paradigm. Am J Chin Med 1993;21:91–101.
92. Shanghai College of Traditional Medicine. Acupuncture, A Comprehensive Text. Transl. by O'Connor J, Bensky D. Seattle: Eastland Press, 1987:119–392.
93. Ibid.: 409–414.
94. Ibid.:515–519.
94a. Ibid.:46.
94b. Ibid.:119–122.
95. Shanghai College of Traditional Chinese Medicine (Zhen Guo Yang). Cross sectional atlas of commonly used acupuncture points of the arm and leg. Transl. by Holland A. (1989).
96. Shanghai Institute of Physiology. Electromyographic activity produced locally by acupuncture manipulation. (In Chinese) Chin Med J 1973;153: 532–535.
97. Shanghai Medical University, Human Anatomy Department. A relationship between points of meridian and peripheral nerves: acupuncture anaesthetic theory study. Shanghai: Shanghai People's Publishing House, 1973: 251–264.
97a. Sherman K J. Characteristics and complaints of patients seeking therapy. J Alt Compl Med 1997; 3:213–214.
97b. Shiro J A, Chan B M C, Roswit W T, Kassner P D, Pentland A P, Hemler M E, Eisen A Z, Kupper T S. Integrin 2 1(VLA-2) mediates reorganization and contraction of collagen matrices by human cells. Cell 1991;67:403–410.
98. Soulie de Morant G. Chinese acupuncture. English ed. Brookline: Paradigm Publications, 1994: 9–15.
99. Ibid.: 162–165.

99a. Ibid.: 335.
100. Stryker W S, Gunn R A, and Francis D P. Outbreak of Hepatitis B associated with acupuncture. J Fam Practice 1986; 22:155–158.
101. Stux G, Pomeranz B. Acupuncture textbook and atlas. Berlin: Springer-Verlag, Berlin, 1987.
102. Stux G, Pomeranz B. Basics of acupuncture, 3rd ed. Berlin: Springer-Verlag, 1995: 30–40.
102a. Turner J A, Deyo R A, Loeser J D, Von Korff M, Fordyce W E. The importance of placebo effects in pain treatment and research. JAMA 1994; 271:1609–1614.
103. Vincent C A, Richardson P H. The evaluation of therapeutic acupuncture: concept and method. Pain 1986; 24:1–13.
104. Vincent C A, Richardson P H, Black J J, Pither C E. The significance of needle placement site in acupuncture. J Psychosom Res 1989; 33:489–496.
105. Vincent C A, Lewith G. Placebo controls for acupuncture studies. J Royal Soc Med 1995; 88:199–202.
106. Vittecoq D et al. Acute HIV infection after acupuncture treatments. N Engl J Med 1989; 320: 250–251.
107. Walter and Israel. General pathology. Edinburgh: Churchill Livingstone, 1987.
108. Wang K, Yao S, Xian Y, Hou Z. A study on the receptive field of acupoints and the relationship between characteristics of needling sensation and groups of afferent tissues. Scientia Sinica 1985; 28:963–971.
108a. Weaver J C, Astumian R D. The response of living cells to very weak electric fields: the thermal noise limit. Science 1990;247:459–462.
108b. Wilson E, Sudhir K, Ives H E. Mechanical strain of rat vascular smooth muscle cells is sensed by specific extracellular matrix/integrin interactions. J Clin Invest 1995; 96:2364–2372.
109. Winer B J, Brown B R, Michels K M. Statistical principles and experimental design. New York: McGrawHill, 1991.
110. Wright R S, Kupperman J L, Liebhaber M I. Bilateral tension pneumothoraces after acupuncture. West J Med 1991; 154:102–103.
111. Worsley J R. Traditional Chinese Acupuncture Volume 1: Meridians and points. Tisbury: Element Books, 1982.
112. Worsley J R. Traditional Acupuncture Volume 2: Traditional diagnosis. Royal Leamington Spa: College of Traditional Acupuncture, 1990.

Chinese Classics
113. Ling shu or the spiritual pivot. Transl. by Wu Jing Nuan. Honolulu: University of Hawaii Press, 1993
114. Ode to the golden needle. In: The golden needle and other odes of traditional acupuncture. Transl. by Bertschinger R. Edinburgh: Churchill Livingstone, 1991: 61–72.
115. Ode to the streamer out of the dark. In: The golden needle and other odes of traditional acupuncture. Transl. by Bertschinger R. Edinburgh: Churchill Livingstone, 1991:17–53.

What is claimed is:

1. A needling device comprising:

(a) an elongated encasement;

(b) a needle mount slidingly mounted within said elongated encasement and adapted to receive and hold a needle; and (c) at least one mounted rotary actuator mounted within said encasement and adapted to impart rotational motion to said needle mount.

2. A needling device as in claim 1, wherein said at least one rotary actuator includes a motor.

3. A needling device as in claim 1, wherein said needle mount includes a collet clamp.

4. A needling device as in claim 1, wherein said needle mount includes a collet clamp adapted to receive and hold the blunt end of an acupuncture needle.

5. A needling device as in claim 1, wherein said needle mount is adapted to establish electrical continuity with a needle held by said needle mount such that EMG signals may be detected using the needle as an EMG probe.

6. A needling device as in claim 5, further comprising a switch configured to establish and break the electrical continuity.

7. A needling device as in claim 5, further comprising an EMG amplifier further configured to amplify EMG signals and to transmit the signals to an analog power meter.

8. A needling device as in claim 1, further comprising a contacting extension at an end of said encasement for resting against a subject to stabilize the device during needle insertion.

9. A needling device as in claim 8, wherein said extension includes a loadsensor for detecting and generating an output indicative of the amount of force with which the needling device is being held against the subject.

10. A needling device as in claim 1, further comprising at least one linear actuator.

11. A needling device as in claim 1, further comprising at least one activation switch configured to provide power to said at least one rotary actuator.

12. A needling device as in claim 10, wherein said at least one linear actuator includes a miniature DC servomotor.

13. A needling device as in claim 10, wherein said at least one linear actuator is coupled to said needle mount by a lead screw device.

14. A needling device as in claim 1, wherein said at least one rotary actuator includes a miniature DC servomotor.

15. A needling device as in claim 10, wherein at least one of said at least one linear actuator and said at least one rotary actuator is configured as a stepper motor.

16. A needling device as in claim 1, further comprising a linear variable displacement transducer mounted in said elongated encasement for providing a measure of axial needle position with respect to a needle held by said needle mount.

17. A needling device as in claim 1, further comprising a uniaxial strain gauge loadcell positioned to measure the axial load applied to said at least one rotary actuator during at least one of needle insertion and needle retraction.

18. A needling device as in claim 1, further comprising a computerized control system in communication with said device to control said at least one rotary actuator in a manner that permits insertion, manipulation, and retraction of a needle held by said needle mount.

19. A needling device as in claim 18, further comprising: at least one activation switch mounted to the needling device; wherein said computerized control system is configured to control insertion, manipulation, and retraction of the needle by activating said at least one activation switch.

20. A needling device as in claim 19, further comprising:

(a) a uniaxial strain gauge loadcell positioned to measure the axial load applied to said at least one rotary actuator during at least one of needle insertion and needle retraction; and (b) an activation switch that generates a signal instructing said computerized control system to zero said loadcell in a starting position and to begin sampling data.

21. A needling device as in claim 18, wherein said computerized control system is programmed to continuously monitor parameters of needle insertion and to terminate operation of the needling device if one or more parameters exceeds at least one predetermined threshold.

22. A needling device as in claim 21, wherein said at least one predetermined threshold includes:

(a) the needle being inserted more than about 2 mm deeper than a target depth; or (b) a maximum insertion or retraction force reaching 3.9 N.

23. A needling device as in claim 8, wherein the axial travel of said needle mount is limited by mechanical contact of said needle mount with said contacting extension.

24. A needling device as in claim 1, further comprising a control and data acquisition system adapted to electrically communicate with the needling device using optical isolation amplifiers.

25. A method of using a needling device, comprising the steps of:

(a) providing a needling device as recited in claim 1; and (b) using the needling device to complete at least one step selected from the group consisting of (i) inserting a needle into a subject, (ii) manipulating the needle, and (iii) withdrawing the needle;

wherein said using step is performed to obtain at least one of physical and electrical data.

26. A method as in claim 25, wherein said using step is performed as a component of a therapeutic regimen.

27. A method as in claim 25, wherein said using step is performed as a component of a diagnostic regimen.

28. A method as in claim 26, wherein said using step includes inserting a needle into an acupuncture point of a subject.

29. A method as in claim 26, wherein said using step is performed to elicit needle grasp.

30. A method as in claim 26, wherein said using step is performed to elicit de qi.

31. A method as in claim 25, further comprising:

(c) measuring at least one of physical and electrical parameters associated with any step completed in (b); and (d) comparing said at least one of physical and electrical parameters with a corresponding one of normal physical and electrical parameters to detect the presence of any adverse medical conditions.

32. A method as in claim 25, further comprising:

(c) measuring at least one of physical and electrical parameters associated with any step completed in (b).

33. A method of using a needling device, comprising:

(a) providing a needling device; and (b) using the needling device to complete at least one step selected from the group consisting of (i) inserting a needle into a subject, (ii) manipulating the needle, and (iii) withdrawing the needle;

wherein said needling device includes a shaft, a needle grip mounted at an end of said shaft, a needle mounted in said needle grip and adapted for in vivo use in an animal or a human, and at least one mechanism selected from the group consisting of (i) mechanism for providing an output indicative of retraction force coupled to said shaft or said needle grip and (ii) mechanism for providing an output indicative of torque caused by rotation of said needle coupled to said shaft or said needle grip.

34. A method of using a needling device, comprising:

(a) providing a needling device; and (b) using the needling device to complete at least one step selected from the group consisting of (i) inserting a needle into a subject, (ii) manipulating the needle, and (iii) withdrawing the needle;

wherein said needling device includes a shaft, a needle grip mounted at an end of said shaft, a needle mounted in said needle grip and adapted for in vivo use in an animal or a human, and a force indicator coupled to said shaft or said needle grip.

35. A needling device comprising:

(a) an elongated encasement;

(b) a needle mount slidingly mounted within said elongated encasement and adapted to receive and hold a needle;

(c) at least one linear actuator mounted within said encasement and adapted to impart linear motion to said needle mount; and (d) at least one rotary actuator mounted within said encasement and adapted to impart rotational motion to said needle mount.

36. A needling device as in claim 35, wherein said at least one linear actuator includes a miniature DC servomotor.

37. A needling device as in claim 35, wherein said at least one linear actuator is coupled to said needle mount by a lead screw device.

38. A needling device as in claim 35, wherein at least one of said at least one linear actuator and said at least one rotary actuator is configured as a stepper motor.

39. A needling device comprising:

(a) an elongated encasement;

(b) a needle mount slidingly mounted within said elongated encasement, said needle mount adapted to receive and hold a needle and adapted to establish electrical continuity with the needle held by said needle mount such that EMG signals may be detected using the needle as an EMG probe;

(c) a switch configured to establish and break the electrical continuity between said needle mount and the needle; and (d) at least one actuator selected from the group consisting of (i) a linear actuator mounted within said encasement and adapted to impart linear motion to said needle mount and (ii) a rotary actuator mounted within said encasement and adapted to impart rotational motion to said needle mount.

* * * * *